United States Patent [19]

Fields et al.

[11] 4,108,850

[45] Aug. 22, 1978

[54] POSITIVE-WORKING IMMOBILE PHOTOGRAPHIC AZO COMPOUNDS

[75] Inventors: Donald Lee Fields, Rochester; Richard Paul Henzel, Webster; Philip Thiam Shin Lau; Richard Allan Chasman, both of Rochester, all of N.Y.

[73] Assignee: Eastman Kodak Company, Rochester, N.Y.

[21] Appl. No.: 679,623

[22] Filed: Apr. 23, 1976

Related U.S. Application Data

[62] Division of Ser. No. 511,568, Oct. 2, 1974, Pat. No. 3,980,499.

[51] Int. Cl.$^2$ .................. C07C 107/00; C07C 107/04; C09B 43/12

[52] U.S. Cl. .................................... 260/162; 260/144; 260/152; 260/155; 260/156; 260/159; 260/160; 260/166; 260/167; 260/169; 260/173; 260/174; 260/175; 260/194; 260/195; 260/196; 260/197; 260/198; 260/199; 260/200; 260/201; 260/202; 260/203; 260/206; 260/207; 260/207.1

[58] Field of Search ............... 260/196, 199, 197, 198, 260/201, 202, 194, 195, 200, 203, 206, 207, 207.1, 155, 156, 159, 160, 162, 166, 169, 173, 174, 144, 167, 175, 152

[56] References Cited

U.S. PATENT DOCUMENTS 3,443,940 5/1969 Bloom et al. ............................. 96/3

*Primary Examiner*—Charles F. Warren
*Attorney, Agent, or Firm*—G. E. Battist

[57] ABSTRACT

Photographic elements, processes for forming images in photographic elements and new compounds are disclosed. Generally, the invention relates to immobile compounds which can be used to provide positive images from negative recording-developing photographic materials such as negative silver halide emulsions. The compounds contain a photographically useful group such as a dye or dye precursor and are capable of releasing said photographically useful group under alkaline conditions, and are also capable of reaction with an oxidized silver halide developing agent before substantial release of said photographically useful group occurs, to provide a reaction product having a substantially lower rate of release of said photographically useful group. In specific embodiments, the compounds of this invention contain an electrophilic cleavage group located in the linkage between a ballast group and a photographically useful moiety wherein said electrophilic cleavage group is a carbamic acid derivative.

47 Claims, No Drawings

POSITIVE-WORKING IMMOBILE PHOTOGRAPHIC AZO COMPOUNDS

This is a division of application Ser. No. 511,568, filed Oct. 2, 1974 now U.S. Pat. No. 3,980,479.

This invention relates to new compounds, photographic elements and processes of forming image records in photographic elements. In one aspect, this invention relates to image dye-providing materials which are immobile or ballasted compounds as incorporated into photographic elements. In another aspect, this invention relates to dye image-providing materials which can be used in image-transfer film units.

It is known in the art to use image dye-providing materials in photographic elements such as image-transfer film units. Image dye-providing materials which are initially mobile in the film units have been employed, for example, such as the mobile couplers and developers disclosed in Land, U.S. Pat. No. 2,698,244 issued Dec. 28, 1954, where a dye is synthesized in the receiver layer. Preformed mobile dyes which reacted with mobile oxidized color developers are disclosed in U.S. Pat. No. 2,774,668. Further disclosures of the use of mobile preformed dyes are found in Rogers, U.S. Pat. No. 2,983,606 issued May 8, 1961. However, the initially mobile dye image-providing materials have certain disadvantages in photographic elements: they can diffuse prematurely to adjacent layers affecting inter-image color reproduction and they remain reactive when diffusing through adjacent layers after development where they can react to cause drop-off in color scales, and the like.

Image dye-providing materials which are initially immobile in a photographic element or are ballasted overcome several of the problems with initially mobile compounds. The dyes could be temporarily ballasted by a heavy counter ion such as a barium salt as disclosed in Yutzy, U.S. Pat. No. 2,756,142 issued July 24, 1956. The dyes can contain a removable ballast group as described in Whitmore Canadian Pat. No. 602,607 issued Aug. 2, 1960, U.S. Pat. No. 3,227,552 by Whitmore issued January 4, 1966, U.S. Pats. No. 3,628,952, 3,728,113, 3,725,062, and the like. Compounds which undergo intramolecular ring closure upon oxidation to split off a dye are disclosed in U.S. Pat. Nos. 3,443,939, 3,443,940 and 3,443,941, all issued May 13, 1969, and U.S. Pat. No. 3,751,406 issued Aug. 7, 1973. Improved initially immobile compounds which undergo a redox reaction followed by alkali cleavage to split off a dye or dye precursor moiety are disclosed in Fleckenstein et al, U.S. Ser. No. 351,673 filed Apr. 16, 1973, and published as B351673 on Jan. 28, 1975. However, these image dye-providing materials are generally limited in application by the fact that the dye is released in the areas where oxidation takes place. Thus, direct-positive silver halide emulsions or some other reversing mechanism, such as use of development nuclei in layers adjacent the recording layer, are used if a positive transfer image is desired.

Positive-working immobile compounds for use in photographic elements are the subject of Hinshaw et al, U.S. Ser. No. 326,628 filed Jan. 26, 1973 now abandoned and refiled on Dec. 20, 1974, now U.S. Pat. No. 3,980,479 issued Sept. 14, 1976, as U.S. Ser. No. 534,966. The positive-working compounds disclosed therein overcome many of the inherent limitations of the initially immobile compounds of the prior art. Generally, the compounds of Hinshaw et al. are immobile ballasted compounds which can undergo a reaction such as a nucleophilic displacement reaction in their reduced form to release a mobile and diffusible photographically useful group, and said compounds can be oxidized, such as by a redox reaction in a photographic element, to lower substantially the rate of release of said photographically useful groups. While several types of compounds are described which generally function as positive-working immobile compounds, it is desirable to provide additional compounds which are easier to synthesize, produce released photographically useful moieties such as dyes which have better properties in the photographic element, have improved nucleophilic-electrophilic group combinations to provide better release systems, etc.

We have now discovered a new class of compounds which can be used in photographic elements and in processes for producing image records which overcome many inherent limitations of the immobile compounds known in the art prior to Hinshaw et al, and offer certain improvements over the specific compounds disclosed by Hinshaw et al.

The compounds of this invention are initially immobile compounds which contain an electrophilic cleavage group linking a photographically useful moiety to a ballast moiety and said compounds also contain a nucleophilic group which is capable of (1) interaction with said electrophilic cleavage group to release a diffusible photographically useful substance under alkaline conditions and (2) reacting with an oxidized silver halide developer before substantial release of said photographically useful substance occurs to lower substantially the rate of release of said photographically useful group under alkaline conditions, wherein said electrophilic cleavage group contains a carbamic acid derivative. The carbamic acid derivative as referred to herein has the formula:

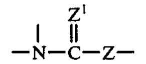

wherein Z is an oxygen atom, an amino group, a sulfur atom or a selenium atom and $Z^1$ is an oxygen atom or a sulfur atom. Typical useful carbamic acid derivatives include carbamic esters such as carbamate ester, thiocarbamate ester, dithiocarbamate ester and the like, and carbamic amides such as a urea, a thiourea and the like. It is understood that, when reference is made herein to linkages through a carbamic acid derivative, N, C and Z in the above formula are in the linkage of atoms connecting the respective moieties, and preferably said carbamic acid derivative is positioned in said linkage so that N in said formula is between the carbonyl group of said formula and the nucleophilic group in said compound.

In certain embodiments, the compounds of this invention contain an aromatic ring, including carbocyclic groups such as a benzene ring and heterocyclic groups, having an oxidizable nucleophilic group substituent on a carbon atom of said ring and ortho thereto a substituent containing a carbamic ester derivative located to facilitate intramolecular nucleophilic displacement with said nucleophilic group, and wherein said compound contains a ballast moiety linked to a photographically useful group through said carbamic acid derivative. In certain instances, it is possible to have two separate nucleophilic groups on said aromatic ring, each of which has an ortho substituent as described above; a highly efficient compound is provided since oxidation of the nucleophilic groups can prevent the release of two molecules of a photographically useful substance such as an image dye.

Although it is not intended to limit the reaction mechanism to any particular theory or reaction mechanism, it is believed that the following chemical reactions take place according to the process of this invention with reference to simplified formulae for clarity:

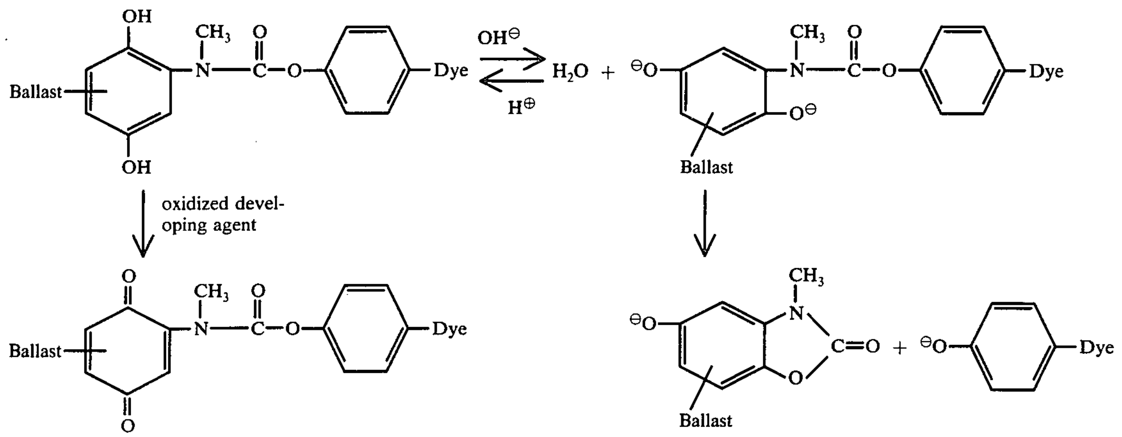

The photographically useful moiety such as a dye is released where the nucleophilic group, such as the OH on the hydroquinone, can attack the carbamate ester linkage. However, when the nucleophilic group is oxidized, such as when the hydroquinone is oxidized to form a quinone, nucleophilic displacement is prevented.

We have found that the compounds of this invention which contain the carbamic acid derivative can be prepared more easily with fewer difficult procedural steps than corresponding prior compounds. Moreover, the carbamic acid derivative provides a linkage which can be readily cleaved by intramolecular displacement, but is relatively stable to external attack by alkali. In addition, the carbamic acid derivative linkage-nucleophilic group combinations of this invention provide good compounds where the leaving group (atom at the cleavage point) can be an oxygen atom or a sulfur atom whereby photographically useful substances, such as dyes, which are released by nucleophilic displacement will have improved properties such as solubility properties, mordanting properties, etc.

Where the compounds of this invention are used in photographic elements, they generally have a rate of release of the photographically useful group which is slower than the rate at which they react with oxidized silver halide developing agent, but faster than the rate of fog formation in the unexposed areas of the photographic element. The rate of fog formation can be controlled by using slowly developing silver halide emulsions or the use of addenda which restrain or suppress further development include the antifoggants, development restrainers and hydrolyzable precursors thereof.

The compounds of this invention are especially useful in photographic systems where the photographically useful group is an image dye-providing group such as a dye or dye precursor. When the compounds are incorporated in a photographic element in association with a silver halide emulsion, the compounds function to provide a positive transfer of image dye-providing substance with a negative silver halide emulsion. Since the compounds are ballasted or immobile as incorporated in the photographic element, additional parameters of control are provided with resultant improved image quality. In certain preferred embodiments, a dye can be released which can diffuse through adjacent layers with a minimum of interaction with silver halide or other compounds in the adjacent layers. Still another advantage is attained in certain embodiments where a shifted or preformed dye can be released from an immobile compound associated with a negative silver halide emulsion to produce an image record without the necessity of oxidation reactions on the receiver sheet, such as is required with oxichromic compounds, leuco compounds, color couplers and the like, which generally require oxidation reactions to provide the image dye.

In one highly preferred embodiment, this invention relates to immobile compounds containing a hydroquinone moiety or an alkali-labile precursor therefor having ortho to at least one hydroxy group a substituent which contains a carbamic acid derivative located to facilitate intramolecular nucleophilic displacement with said hydroxy group and wherein said compound contains a ballast moiety linked to a photographically useful moiety through said carbamic acid derivative.

In another embodiment, this invention relates to photographic elements comprising a support having thereon at least one layer containing a photographic recording material such as silver halide having associated therewith an intramolecular nucleophilic displacement compound. Preferably, the intramolecular nucleophilic displacement compound comprises an image dye-providing group which is a dye, including shifted dyes, or a dye precursor, such as an oxichromic compound or a color coupler and the like.

In a preferred embodiment, this invention relates to photographic elements which comprise a support having thereon a red-sensitive silver halide emulsion having associated therewith an intramolecular nucleophilic displacement compound comprising a cyan image dye-providing moiety, a layer containing a green-sensitive silver halide emulsion having associated therewith an intramolecular nucleophilic displacement compound which comprises a magenta image dye-providing moiety, and a layer containing a blue-sensitive silver halide emulsion having associated therewith an intramolecular nucleophilic displacement compound which comprises a yellow image dye-providing moiety.

In another highly preferred embodiment, this invention relates to image-transfer systems which comprise a silver halide emulsion having associated therewith an intramolecular nucleophilic displacement compound which preferably comprises an image dye-providing moiety which is a preformed dye or a shifted dye.

In a specific embodiment in accordance with this invention, a photographic film unit is provided which is adapted to be processed by passing said unit between a pair of juxtaposed pressure-applying members, such as would be found in a camera designed for in-camera processing. The unit comprises (1) a photosensitive element which contains a silver halide emulsion having associated therewith an immobile intramolecular nucleophilic displacement compound, (2) an image dye-receiving layer, (3) means for discharging an alkaline processing composition within the film unit, such as a rupturable container which is adapted to be positioned during processing of the film so that a compressive force applied to the container by the pressure-applying members will effect a discharge of the container's contents within the film, and (4) a silver halide developing agent which is soluble in alkaline processing composition located within said film unit.

In still another embodiment, this invention relates to a new process comprising (1) applying an alkaline processing composition to an imagewise-exposed photographic element comprising a support having thereon at least one layer containing a photographic recording material, such as silver halide, and at least one layer thereon containing a nondiffusible compound having a photographically useful moiety wherein said compound is capable of releasing said photographically useful group under alkaline conditions, and is also capable of reaction with an oxidized developing agent for said photographic recording material, wherein the reaction product has a substantially lower rate of release of the photographically useful group, and (2) providing said developing agent for said photographically recording material during application of said alkaline processing composition under conditions to effect imagewise release of said photographically useful moiety as an inverse function of development of said photographic recording material, whereby an image record is obtained in said photographic element.

In a highly preferred embodiment, this invention relates to a photographic transfer process comprising:

(a) treating a photographic element prepared in accordance with this invention with an alkaline processing composition in the presence of a silver halide developing agent to effect development of each of the exposed silver halide emulsion layers, thereby oxidizing the developing agent;

(b) the oxidized developing agent cross-oxidizing said immobile compound according to this invention as a function of development before substantial release of said photographically useful group occurs whereby said cross-oxidation substantially reduces the rate of release of said photographically useful group;

(c) maintaining said photographic element in an alkaline medium for a time sufficient to release said photographically useful group from the immobile compound which has not reacted with said developing agent; and (d) at least a portion of said photographically useful compound transferring to an adjacent layer to provide a positive image record.

In this embodiment, the photographically useful compound is preferably an image dye or image-dye precursor. The image-transfer process is preferably carried out in an integral negative-receiver image-transfer element where the image-receiving layer and the photographic recording layers are coated on the same support, preferably with an opaque layer which is reflective to light located between the receiver layer and the recording layers; the alkaline processing composition can be applied between the outer recording layers of the photographic element and a cover sheet which can be transparent and superposed before exposure.

Positive retained images can be readily obtained in photographic elements of this invention, and especially those elements which contain an immobile compound in accordance with this invention which contains a hydrolyzable precursor for the nucleophilic group. The elements can be first developed with a developing agent in an environment having a pH below that necessary to hydrolyze the precursor for said nucleophilic group; then the photographic element can be fogged, light-flashed, etc., and developed in a solution having a pH sufficiently high to effect intramolecular nucleophilic displacement of said immobile compounds.

Generally, the immobile compounds contain a nucleophilic group and an electrophilic group so chosen that, when the compound is incorporated in a photographic element, the rate of oxidation of the nucleophilic group is substantially greater than the rate of intramolecular nucleophilic displacement or cleavage at the electrophilic group. Since the rate of oxidation is substantially greater than the rate of nucleophilic displacement, an imagewise pattern of the more mobile group will be produced after displacement; i.e., where said compound contains an image dye which is diffusible after nucleophilic displacement, an image record can be observed in layers adjacent the layer of initial location of said compound. Generally, there will be at least twice as much and preferably at least ten times more of said nucleophilic displacement in the unoxidized areas than in the oxidized areas, and preferably there is substantially no nucleophilic displacement in the areas of said photographic element where all of said compound is oxidized. Where dyes or dye precursors are released, generally at least two times and preferably at least five times more dye or dye precursor is released in the unoxidized areas than in the oxidized areas.

In certain highly preferred embodiments, the compounds of this invention contain a group which is a precursor for the oxidizable nucleophilic group, for example, a hydrolyzable precursor for an hydroxyl group. In compounds where the nucleophilic group is blocked, the possibility of premature reactions' releasing the photographically useful moiety is substantially eliminated. Moreover, by controlling the development conditions, the availability of the nucleophilic group for reaction and intramolecular nucleophilic displacement can be delayed, if desired.

Generally, the compounds of this invention are defined as intramolecular nucleophilic displacement compounds. The term "intramolecular nucleophilic displacement" is understood to refer to a reaction in which a nucleophilic center attached to a compound reacts at another site on said compound, which is an electrophilic center, to effect displacement of a group or atom attached to said electrophilic center. Generally, the intramolecular nucleophilic displacement compounds are those compounds which have the nucleophilic group and the electrophilic center juxtaposed by the three-dimensional configuration of the molecule to promote close proximity of the groups whereby the reaction can take place. In accordance with this invention, the nucleophilic groups and electrophilic groups are located on compounds to provide favorable juxtaposition of the group wherein a cyclic organic ring or a transient cyclic organic ring can be easily formed by intramolecular reaction of the nucleophilic group at the electrophilic center. Cyclic groups can be generally formed with 3–8 atoms thereon, and preferably in accordance with this invention the nucleophilic group and the electrophilic group are positioned on a compound where they can form a 5- to 8-membered ring, and more preferably a 5- or 6-membered ring. Intramolecular nucleophilic displacement occurs with the compounds of this invention when the compound is in the reduced state and the rate of nucleophilic displacement appears to be substantially reduced and preferably eliminated when the nucleophile is oxidized. The mechanism of the above compounds as described is believed to be different in kind from compounds known in the art prior to Hinshaw et al which are oxidized to provide an electrophilic center with subsequent cleavage of a dye.

Compounds which undergo intramolecular nucleophilic displacement can generally be readily distinguished from compounds which undergo intermolecular nucleophilic displacement by observing the reaction characteristics of the respective compounds. In one test, a mixture of compounds according to this invention, which have been modified by blocking the nucleophilic groups on some and using a different, readily distinguishable release group on others, will undergo release of the photographically useful moiety much slower from the blocked compounds than from the unblocked compounds, especially when carried out in an aqueous alkaline medium, i.e., such as an alkali-permeable hydrophilic colloid saturated with mildly alkaline solutions.

In certain embodiments, the compounds useful in accordance with the invention have the structure:

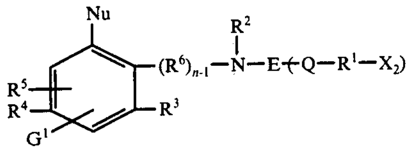

wherein Nu is an oxidizable nucleophilic group such as an hydroxy group (—OH), a primary amino group (—$NH_2$), a secondary amino group, an hydroxylamino group, a sulfonamido group, and the like, including precursors for said nucleophilic group and preferably alkali-labile precursors such as —O—$R^7$, —$NHR^7$ and the like wherein $R^7$ is an alkali-labile group such as a formyl group, acyl groups, carbobenzoxy groups, oxalate groups, halogenated acetyl groups and the like containing from 1 to 15 carbon atoms, including cyclic groups formed with substituents for $R^5$ when it is ortho to Nu; $G^1$ is a dialkylamino group, or any of the substituents defined for Nu, including cyclic groups formed with $R^4$ or $R^3$ and preferably $G^1$ is para to Nu; E is an electrophilic group which can be carbonyl —CO— or a thiocarbonyl —CS— group and is preferably carbonyl; Q is a bivalent group providing a mono atom linkage between E and $R^1$ wherein said mono atom is a monometallic atom of group VA or VIA of the periodic table in its $-2$ or $-3$ valence state, such as a nitrogen atom, an oxygen atom, a sulfur atom, a selenium atom and the like, wherein said atom provides two covalent bonds linkage E to $R^1$, and when it is a trivalent atom it can be mono-substituted with a hydrogen atom, an alkyl group containing from 1–10 carbon atoms including substituted alkyl groups, aromatic groups containing 5–20 carbon atoms including aryl groups and substituted aryl groups and the like; $R^6$ is an alkylene group containing from 1 to 3 carbon atoms in the linkage including alkylene groups having substituents thereon, and preferably is an alkylene group containing 1 carbon atom in the bivalent linkage; $n$ is an integer of 1 or 2; $R^1$ can be an aromatic group containing from 6 to 20 carbon atoms including heterocyclic groups, for example, groups containing a nucleus such as pyridine, isoquinoline and the like, or a carbocyclic arylene group which is preferably a phenylene group or a naphthalene group including substituted phenylene and naphthalene groups, or $R^1$ can be an alkylene group containing from 1 to 12 carbon atoms, including substituted alkylene groups and the like; $R^2$ can be an alkyl group containing from 1 to 40 carbon atoms, including substituted alkyl groups and cycloalkyl groups, an aryl group containing from 6 to 40 carbon atoms, including substituted aryl groups and the like, or it can be the substituent $X^1$; $R^3$, $R^4$ and $R^5$ can each be mono atom substituents such as hydrogen or halogen atoms or preferably poly atom substituents such as an alkyl group containing from 1 to 40 carbon atoms, including substituted alkyl groups and cycloalkyl groups, an alkoxy group, an aryl group containing from 6 to 40 carbon atoms, including substituted aryl groups, a carbonyl group, a sulfamyl group, a sulfonamido group and the like, or they can each be the substituent $X^1$ with the provision that $R^3$ and $R^5$ or $R^4$ and $R^5$, when they are on adjacent positions of the ring, may be taken together to form a 5- to 7-membered ring with the remainder of the molecule including bridged rings and the like, and with the provision that, when $R^1$ is an alkylene group, $R^3$ and $R^4$ must be poly atom substituents, and preferably $R^5$ is a poly atom substituent, and when $G^1$ is a nucleophilic group as defined for Nu, the $R^4$ or $R^3$ substituent adjacent G can be the group:

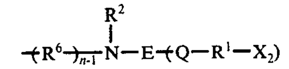

to provide a compound which has multiple groups which can be released by nucleophilic displacement; $X^1$ and $\leftarrow(Q—R^1—X_2)$ can each be a ballasting group of sufficient size to render said compound immobile in an alkali-permeable layer of a photographic element, or a photographically useful moiety, provided one of $X^1$ and $\leftarrow(Q—R^1—X_2)$ is a ballast group and the other is a photographically useful moiety, such as a photographic reagent or preferably is an image dye-providing material such as an image dye or an image-dye precursor; and $R^6$ is selected to provide substantial proximity of Nu to E to permit intramolecular nucleophilic cleavage of Q from E, and is preferably selected to provide 3 to 5 atoms between the atom which is the nucleophilic center of said nucleophilic group and the atom which is the electrophilic center of said electrophilic group, whereby said compound is capable of forming a 5- to 8-membered ring and most preferably a 5- or 6-membered ring upon intramolecular nucleophilic displacement of the group $\leftarrow(Q—R^1—X_2)$ from said electrophilic group.

In one preferred embodiment, Nu in compounds represented by the above formula is an hydroxy group or a precursor therefor and the carbamic acid derivative is a carbamic acid ester. The carbamic ester moiety wherein Q is S or O provides a very effective cleavable group when used in combination with the hydroxy nucleophilic group which is attached directly on the benzene ring.

In another embodiment, Nu in the compounds represented in the above formula is a nucleophilic amino group or a precursor therefor and Q is an amino group, an oxygen atom or a sulfur atom.

In the above formula where $\text{-(}Q—R^1—X_2)$ is the photographically useful moiety, a photographically active group can be made available by Q upon cleavage of $\text{-(}Q—R^1—X_2)$ from the remainder of the compound, i.e., such as where $\text{-(}Q—R^1—X_2)$ forms a mercaptotetrazole and the like. However, where $X^1$ is the photographically useful group, the group can be attached in such a manner that it does not rely upon the cleavage to provide a photographically useful site.

The photographically useful moiety represented by $\text{-(}Q—R^1—X_2)$ or $X^1$ in the above formula can be a silver halide development inhibitor including triazoles and tetrazoles such as a 5-mercapto-1-phenyltetrazole, a 5-methylbenzotriazole, a 4,5-dichlorobenzotriazole and the like, and it can also be an antifoggant including azaindenes such as a tetrazaindene and the like. The compounds which contain releasable silver halide development inhibitors or antifoggants can generally be used in the photographic elements in association with silver halide layers wherein said compound can be incorporated in amounts such as 1 to 100 mg./ft.$^2$ dissolved in a coupler solvent such as diethyl lauramide. When these compounds are incorporated in photographic elements in association with negative silver halide emulsions, a positive imagewise distribution of inhibitor or antifoggant will be produced upon development. Thus, silver development is inhibited or restrained in the low-exposure toe as seen on the H and D curve, but not in the more fully exposed shoulder as seen on the H and D curve. Development inhibition of the unexposed areas is thereby achieved selectively. When the silver halide emulsions also have dye releasers in accordance with this invention associated therewith, the overall effect of the inhibitor or antifoggant is to release more dye in the unexposed regions, improving maximum image-dye density to the image-receiving layer without increasing the amount of dye released in the exposed regions.

The photographically useful moiety represented by $\text{-(}Q—R^1—X_2)$ or $X^1$ can also be a silver halide development accelerator such as a benzyl alcohol, a benzyl $\alpha$-picolinium bromide and the like, a foggant including hydrazines and hydrazides such as an acetylphenylhydrazine and the like, or an auxiliary developer such as a hydroquinone, a 1-phenyl-3-pyrazolidone, ascorbic acid and the like. When these compounds are used in photographic elements in association with silver halide emulsions which also have associated therewith image dye-providing materials in accordance with this invention, the released dye density of all dyes in the unexposed regions would be somewhat reduced by fog development. If however, one layer was unexposed while the other two were given an imagewise exposure, the amount of foggant or development accelerator reaching the unexposed layer from the other two layers would be less where those layers were exposed. Hence, the Dmax of the unexposed layer would increase as a function of exposure of the other two layers. This greatly enhances the saturation of single colors in a photograph.

The nature of the ballasting group in the above compounds is not critical, as long as the portion of the compound on the ballast side of E is primarily responsible for the immobility; the other portion of the molecule on the remaining side of E generally contains sufficient solubilizing groups to render it mobile and diffusible after cleavage. Thus, $X^1$ could be of very low molecular weight if the remainder of the group in the compound confers sufficient insolubility to the compound to render it immobile. However, when $X^1$ or $\text{-(}Q—R^1—X_2)$ serve as the ballast function, they generally comprise long-chain alkyl radicals, as well as aromatic radicals of the benzene and naphthalene series. Typical, useful groups for the ballast function contain at least 8 carbon atoms and preferably at least 14 carbon atoms.

The term "nucleophilic group" as used herein refers to an atom or group of atoms which have an electron pair capable of forming a covalent bond. Groups of this type are sometimes ionizable groups which react as anionic groups. The term "oxidizable nucleophilic group" refers to that nucleophilic group which can be oxidized, thus causing a substantial reduction in the rate of intramolecular nucleophilic displacement relative to the electrophilic group. Generally, the groups are less nucleophilic in character upon oxidation or have a structure which adversely affects the proximity of the nucleophilic center with respect to the electrophilic center.

The nucleophilic group can contain only one nucleophilic center such as the oxygen atom in an hydroxy group, or it can contain more than one nucleophilic center such as in the case of an hydroxylamine group where either the nitrogen atom or the oxygen atom can be the nucleophilic center. Where more than one nucleophilic center is present in the nucleophilic group on the intramolecular nucleophilic displacement compounds of this invention, the nucleophilic attack and displacement will generally occur through the center which is capable of forming the most favored ring structure; i.e., if the oxygen atom of the hydroxylamine group would form a 7-membered ring and the nitrogen atom would form a 6-membered ring, the active nucleophilic center would generally be the nitrogen atom. Typical useful nucleophilic groups include hydroxy groups, primary amino groups, hydroxylamine groups, secondary amino groups such as alkylamino groups and sulfonamido groups including alkylsulfonamido groups and aryl sulfonamido groups, and the like.

The term "electrophilic group" refers to an atom or group of atoms which are capable of accepting an electron pair to form a covalent bond. Typical electrophilic groups are carbonyl groups:

$$(-\overset{\overset{\displaystyle O}{\|}}{C}-),$$

thiocarbonyl:

$$(-\overset{\overset{\displaystyle S}{\|}}{C}-)$$

and the like, where the carbon atom forms the electrophilic center of the group and can sustain a partial positive charge. The term "electrophilic cleavage group" is used herein to refer to the group:

$$(-\overset{|}{N}-E-Q-)$$

wherein E is an electrophilic group and Q is a bivalent leaving group providing a mono atom linkage between E and $-R^1-X_2$ wherein said mono atom is a nonmetallic atom which has a negative valence of 2 or 3. The leaving group is capable of accepting a pair of electrons upon being released from the electrophilic group. Where the nonmetallic atom is a trivalent atom, it can be monosubstituted by a group which can be a hydrogen atom, an alkyl group including substituted alkyl groups and cycloalkyl groups, or an aryl group including substituted aryl groups. Typical atoms useful to form the bivalent linkage in Q are the nonmetallic atoms in groups VA and VIA of the periodic table which are capable of having a negative valence of 2 or 3, such as nitrogen atoms, sulfur atoms, oxygen atoms, selenium atoms and the like.

Bivalent groups are referred to in the above formula definitions. It is understood that the linkage in said bivalent groups refers to the shortest chain of atoms in the respective groups between the covalent bonds shown in said formula.

The term "nondiffusing" used herein has the meaning commonly applied to the term in photography and denotes materials which for all practical purposes do not migrate or wander through organic colloid layers in an alkaline medium, such as gelatin, in the photographic elements of the invention. The same meaning is to be attached to the term "immobile".

The term "diffusible" as applied to the materials of this invention has the converse meaning and denotes materials having the property of diffusing effectively through the colloid layers of the photographic elements in an alkaline medium in the presence of "nondiffusing" materials. "Mobile" has the same meaning.

Typical useful carbamic acid derivatives are as follows:

Compound I

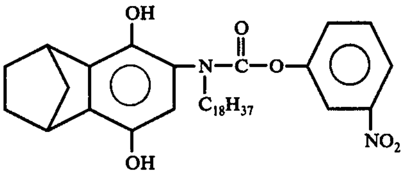

Compound II

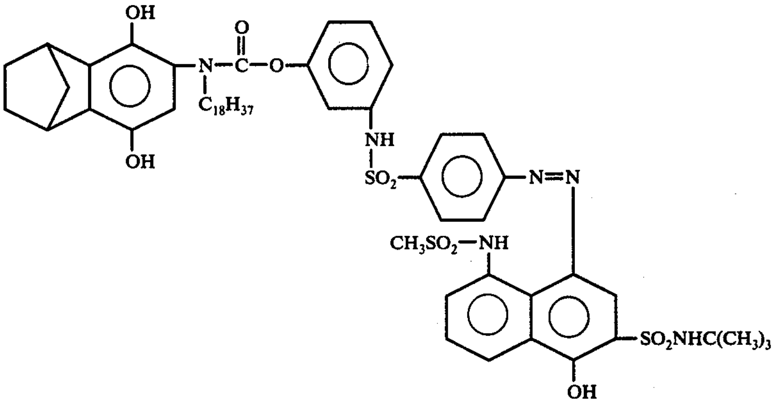

Compound III

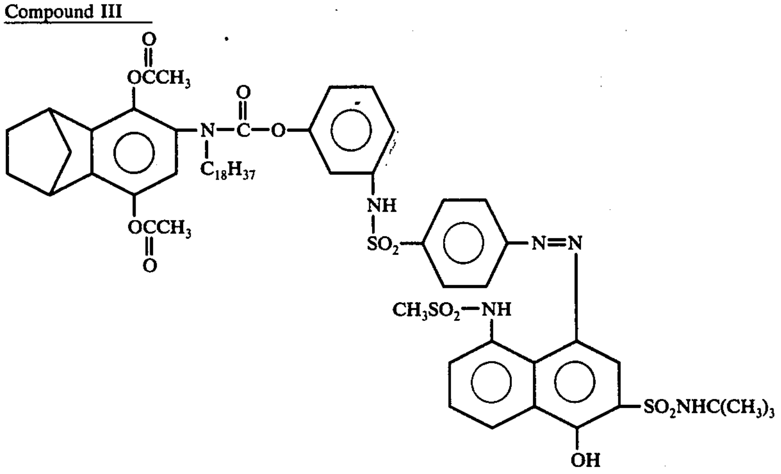

Compound IV

-continued
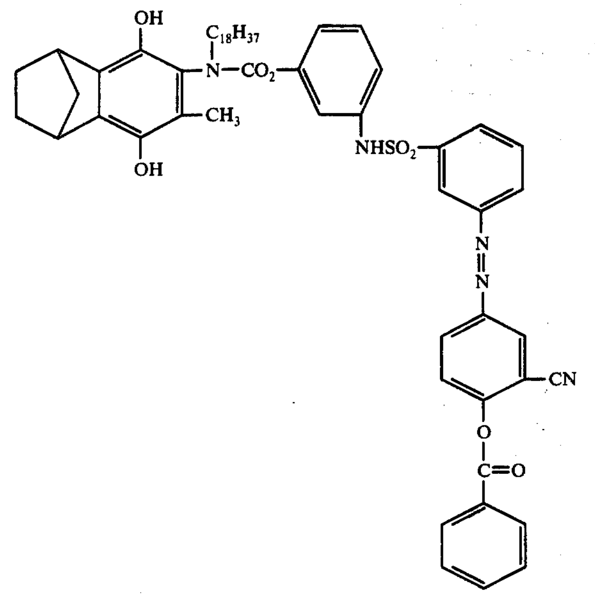
Compound V
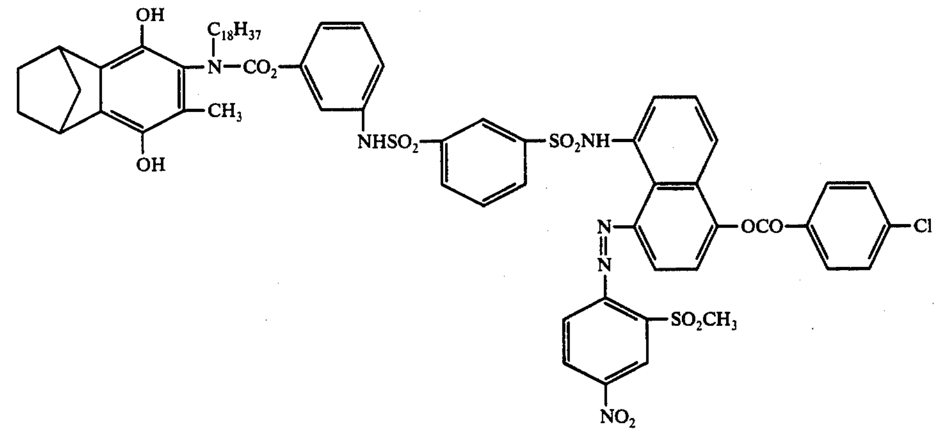
Compound VI
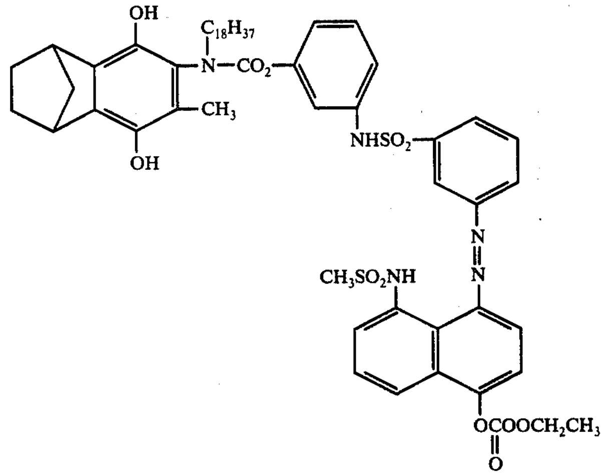
Compound VII

-continued
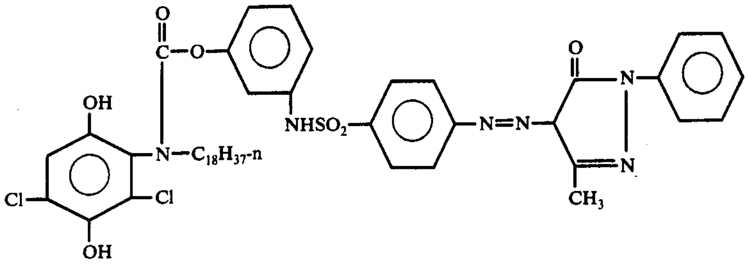
Compound VIII
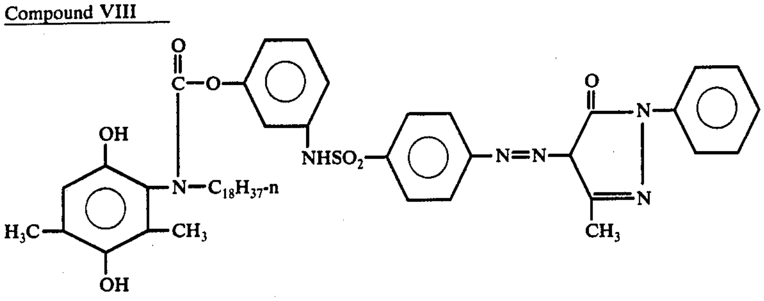
Compound IX
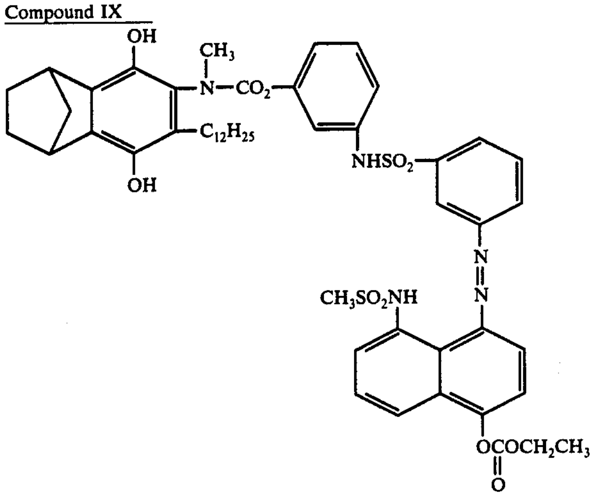
Compound X
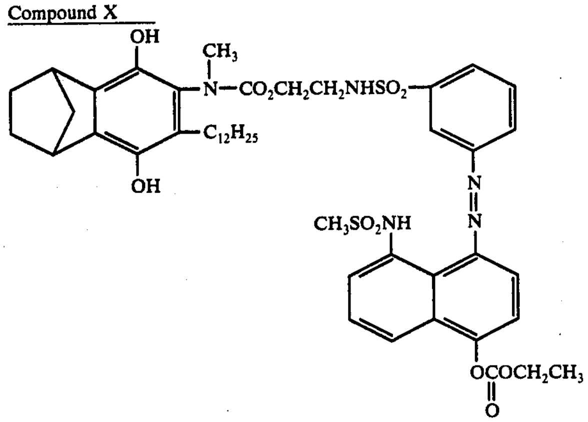
Compound XI
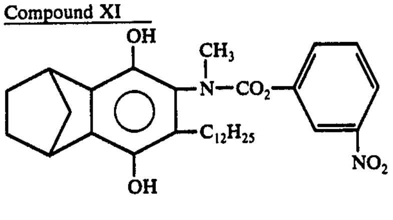

Compound XII
-continued
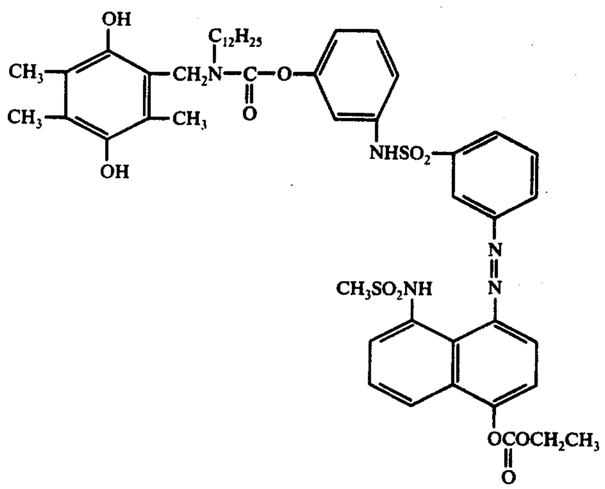
Compound XIII
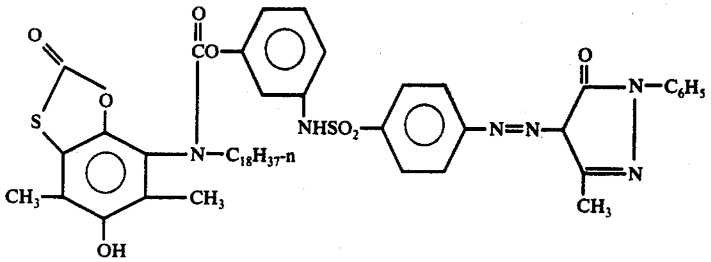
Compound XIV
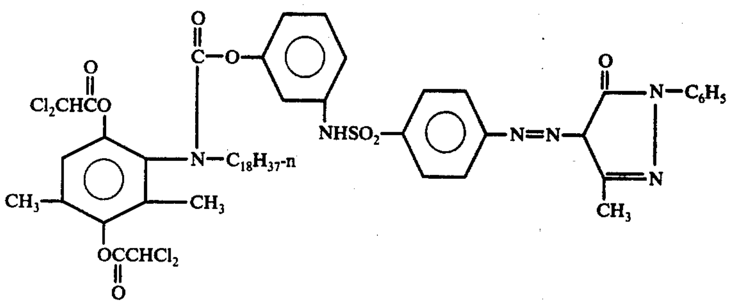
Compound XV
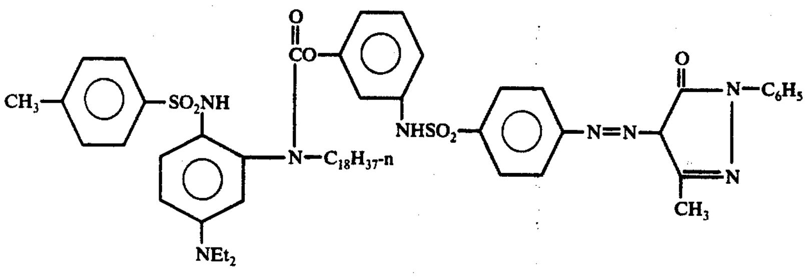

Compound XVI

-continued

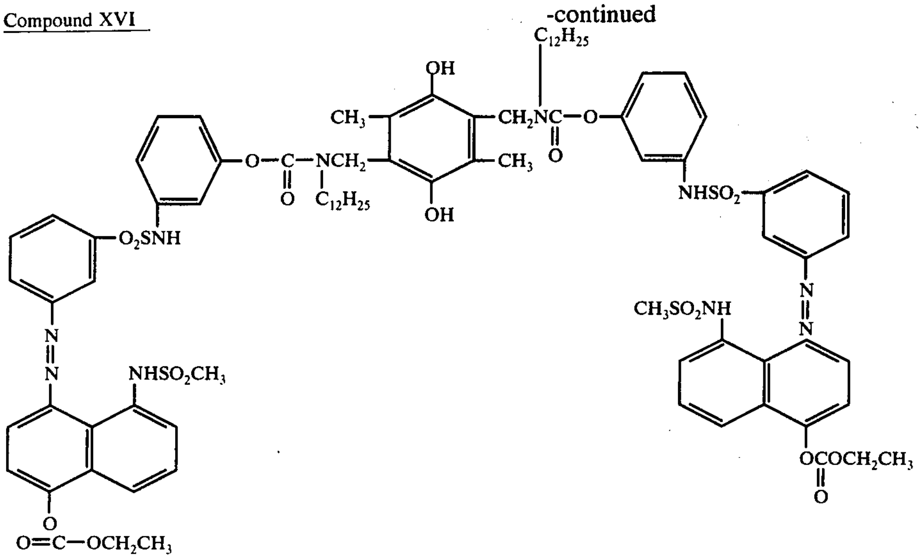

The photographic processes using the immobile compounds are generally carried out in an alkaline medium wherein the nucleophilic displacement can easily take place. In certain embodiments, the processes are carried out in an alkaline medium having a pH of above 12; at a high pH silver halide development proceeds rapidly, dye mobility is generally high and the like. High-pH conditions are especially preferred for image-transfer processes using the compounds of this invention. Moreover, when the compounds containing blocked nucleophilic groups as described above are used in photographic elements, they are generally contacted with an alkaline solution at a pH sufficiently high to cleave the alkali-labile blocking group to provide the nucleophilic group. The compound can then react with an oxidized silver halide developer to reduce the rate of release of the photographically useful group; however, where the compound remains unoxidized, the photographically useful group is released.

The compounds of this invention can be prepared by using conventional techniques used in organic chemistry with proper selection of starting materials. The photographically useful group can be synthesized by methods known in the art with the appropriate linkage and groups for reaction with the remainder of the compound. In a typical procedure for preparing the carbamate acid derivatives of this invention, an aminoquinone is prepared by isomerizing the DielsAlder adduct of cyclopentadiene and tolylquinone by treatment with alumina in alcoholic solvents to produce the unsaturated hydroquinone. The unsaturated hydroquinone is first hydrogenated and then oxidized to give a trisubstituted quinone, which is then converted to an aminoquinone by reaction with a primary amine which preferably contains a long-chain alkyl group thereon to provide a ballast moiety. The desired carbamoyl hydroquinone is then synthesized by catalytically reducing the aminoquinone to an aminohydroquinone, followed by acylation with an appropriate chloroformate which can contain a dye or an intermediate for preparing the dye. It has been found to be very advantageous to position nonreactive groups in the ortho and meta positions of the benzene ring relative to $G^1$ in the above formula and opposite the desired carbamate group substitution in order to obtain high yields of a single product which can be readily purified when reacting with the primary amine above. The blocking of the proper position is believed to be important in obtaining useful yields of the desired products for use in photographic elements.

In the preferred embodiments wherein the compounds of this invention contain a hydroquinone moiety or precursors for a hydroquinone moiety, they can generally be prepared by using in the synthesis compounds such as:

methyl-1,4-benzoquinone
2,5-dimethyl-1,4-benzoquinone
octyl-1,4-benzoquinone
dodecyl-1,4-benzoquinone
2,3,5-trimethyl-1,4-benzoquinone
1,4-naphthoquinone
2-methyl-1,4-naphthoquinone
2-octyl-1,4-naphthoquinone
2-dodecyl-1,4-naphthoquinone
5,8-methano-1,4-naphthoquinone
9,10-o-benzeno-1,4-anthraquinone
2,6-dimethyl-1,4-benzoquinone
2,6-dichloro-1,4-benzoquinone In certain preferred embodiments, the compounds of this invention contain precursors for the nucleophilic groups. Particularly useful precursors are the alkali-labile precursors which undergo hydrolytic cleavage under high-pH conditions to produce the nucleophilic groups. The precursors for the nucleophilic group generally provide better incubation stability and shelf life of the products containing the compounds of this invention. Typical useful alkali-labile hydroquinonyl moieties are as follows:

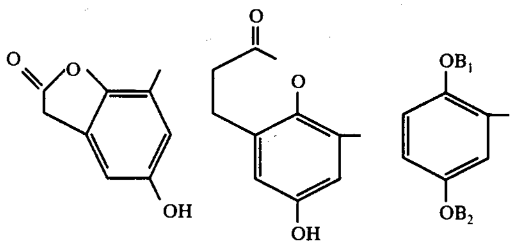

-continued

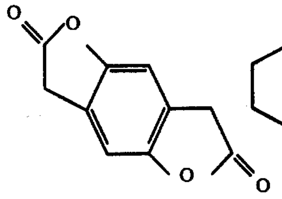

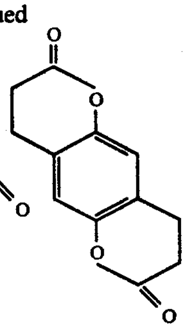

wherein $B^1$ and $B^2$ represent alkali-labile groups such as acyl groups, oxalate groups, carbobenzoxy groups, etc.

In certain preferred embodiments, the compounds of this invention comprise a moiety which is an image dye-providing material. Preferably, the image dye-providing moiety is a preformed dye or a shifted dye. Dye materials of this type are well-known in the art and include dyes such as azo dyes, azomethine (imine) dyes, anthraquinone dyes, alizarin dyes, merocyanine dyes, quinoline dyes, cyanine dyes and the like. The shifted dyes include those compounds wherein the light absorption characteristics are shifted hypsochromically or bathochromically when subjected to a different environment such as a change in pH, reaction with a material to form a complex, tautomerization, reactions to change the pKa of the compound, removal of a group such as a hydrolyzable acyl group connected to an atom of the chromophore as mentioned in Weyerts, U.S. Pat. No. 3,260,597 issued July 12, 1966, and the like. In certain embodiments, the shifted dyes are highly preferred and especially those containing a hydrolyzable group on an atom affecting the chromophore resonance structure, since the compounds can be incorporated directly in a silver halide emulsion layer or even on the exposure side thereof without substantial reduction in the recording light exposure. After exposure, the dye can be shifted to the appropriate color such as, for example, by hydrolytic removal of the acyl group to provide the respective image dye.

In another embodiment, the compounds of this invention contain an image dye-providing moiety which is an image-dye precursor. The term "image-dye precursor" is understood to refer to those compounds which undergo reactions encountered in a photographic imaging system to produce an image dye, such as color couplers, oxichromic compounds, and the like.

When color couplers are present in the compounds of this invention, the coupler can be released in areas where no development occurs and can diffuse to an adjacent layer where they can be reacted with an oxidized color developer such as an oxidized primary aromatic amine to form the image dye. Generally, the color coupler and the color developer are so chosen that the reaction product is immobile. Typical useful color couplers include the pyrazolone couplers, pyrazolotriazole couplers, open-chain ketomethylene couplers, phenolic couplers and the like. Further reference to the description of appropriate couplers is found in Marchant, U.S. Pat. No. 3,620,747 issued Nov. 16, 1971, which is incorporated herein by reference.

The compounds of this invention containing oxichromic moieties can also be advantageously used in a photographic system since they are generally colorless materials due to the absence of an image-dye chromophore. Thus, they can also be used directly in the photographic emulsion or on the exposure side thereof without competitive absorption. Compounds of this type are those compounds which undergo chromogenic oxidation to form the respective image dye. The oxidation can be carried out by aerial oxidation, incorporation of oxidants into the photographic element or film unit, or use of an oxidant during processing. Compounds of this type have been referred to in the art as leuco compounds, i.e., compounds which have no color. Typical useful oxichromic compounds include leuco indoanilines, leuco indophenols, leuco anthraquinones and the like. In certain embodiments, the compounds of this invention contain oxichromic moieties as described in Lestina and Bush, U.S. Pat. No. 3,880,658 issued Apr. 29, 1975, which is incorporated herein by reference.

The compounds described herein have particular application in a diffusion transfer process where it is desired to have a dye entity transferred to an adjacent layer or a receiving element. However, in certain embodiments this invention relates to the release of an imagewise distribution of a diffusible photographically useful compound which is a photographic reagent. Typical useful photographic reagents are known in the art, such as in U.S. Pat. Nos. 3,227,551, 3,698,898, 3,379,529 and 3,364,022, for example, a silver complexing agent, a silver halide solvent, a fixing agent, a toner, a hardener, an antifoggant, a fogging agent, a coupler, a sensitizer, a desensitizer, a developer or an oxidizing agent. In other words, $X_1$ and $(Q-R^1-X_2)$ in the above formula may represent any moiety which, in combination with a hydrogen atom, provides a photographic reagent upon cleavage. Specific examples of useful photographic reagents are provided earlier in the specification.

The compounds of this invention are particularly useful in photographic elements and in photographic processes to provide an imagewise distribution of a photographically useful compound. The photographic element can contain the immobile compounds in association with any photographic material which produces an oxidation product during development which in turn can react with the nucleophilic group on said compound. In certain preferred embodiments, where silver halide emulsions are used as the recording means, the emulsion can be a negative, direct-positive or reversal emulsion and the like which undergo development with a silver halide developing agent to produce oxidized silver halide developer. The oxidized silver halide developing agent can react with the nucleophilic group to produce an addition product and the like, but preferably the silver halide developing agent is so chosen that a simple redox reaction takes place to reduce substantially the rate of release of the photographically useful moiety.

Black-and-white or one-color systems can be made which employ as few as one silver halide emulsion and compounds according to this invention which comprise the required image dye-providing moieties to provide the desired net color effect. Preferably, the compounds of this invention are used in three-color systems such as, for example, photographic elements containing a layer comprising a redsensitive silver halide emulsion having associated therewith an intramolecular nucleophilic displacement compound comprising a cyan image dye-providing moiety, a layer containing a green-sensitive silver halide emulsion having associated therewith an intramolecular nucleophilic displacement compound which comprises a magenta image dye-providing moiety, and a layer containing a blue-sensitive silver halide emulsion having associated therewith an intramolecular nucleophilic displacement compound which comprises a yellow image dye-providing moiety.

The photographic element can be designed to provide an image record in either the image dye-providing material released and made diffusible or in the immobile dye remaining in the initial location attached to the oxidized compound and associated with the respective photographic recording material or, in certain instances, both image records can be used. The residual nondiffusible dye can provide an image record which will be present as a function of silver halide development. The silver and silver halide remaining after development can be removed, if desired, to provide better color properties in the record.

In certain preferred embodiments, the photographic element is used in an image-transfer film unit where the dye image-providing material upon release diffuses to an adjacent image-receiving layer. The compounds of this invention can be used in any image-transfer unit format where either initially mobile compounds are used, such as dye developers, or where the initially immobile compounds are used, such as ballasted redox releasing compounds. Typical useful image-transfer formats are disclosed in U.S. Pat. Nos. 2,543,181, 2,661,293, 2,774,668, 2,983,606, 3,227,550, 3,227,552, 3,309,201, 3,415,644, 3,415,645, 3,415,646 and 3,635,707, Canadian Pat. No. 674,082, Belgian Pat. Nos. 757,959 and 757,960, both issued Apr. 23, 1971, and the like. However, the appropriate silver halide emulsions will have to be used in each format since the present compounds yield a positive image in diffusible dye with a negative recording and developing emulsion.

In certain embodiments, the photographic elements of this invention are processed in the presence of a silver halide developing agent which is preferably a silver halide developing agent which has a redox potential whereby it will cross-oxidize when oxidized with immobile compounds of this invention. Typical useful silver halide developers include hydroquinone compounds such as hydroquinone, 2,5-dichlorohydroquinone, 2-chlorohydroquinone and the like; aminophenol compounds such as 4-aminophenol, N-methylaminophenol, 3-methyl-4-aminophenol, 3,5-dibromoaminophenol and the like; catechol compounds such as catechol, 4-cyclohexylcatechol, 3-methoxycatechol, 4-(N-octadecylamino)catechol and the like; phenylenediamine compounds such as N,N-diethyl-p-phenylenediamine, 3-methyl-N,N-diethyl-p-phenylenediamine, 3-methoxy-N-ethyl-N-ethoxy-p-phenylenediamine and the like; 3-pyrazolidone compounds such as 1-phenyl-3-pyrazolidone, 1-phenyl-4,4-dimethyl-3-pyrazolidone, 4-hydroxymethyl-4-methyl-1-phenyl-3-pyrazolidone, 1-m-tolyl-3-pyrazolidone, 1-p-tolyl-3-pyrazolidone, 1-phenyl-4-methyl-3-pyrazolidone, 1-phenyl-5-methyl-3-pyrazolidone, 1-phenyl-4,4-bis-(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(3-chlorophenyl)-3-pyrazolidone, 1-(4-chlorophenyl)-3-pyrazolidone, 1-(4-tolyl-4-methyl-3-pyrazolidone, 1-(2-tolyl)-4-methyl-3-pyrazolidone, 1-(4-tolyl)-3-pyrazolidone, 1-(3-tolyl)-3-pyrazolidone, 1-(3-tolyl)-4,4-dimethyl-3-pyrazolidone, 1-(2-trifluoroethyl)-4,4-dimethyl-3-pyrazolidone, 5-methyl-3-pyrazolidone and the like; etc. A plurality of developing agents such as those disclosed in U.S. Pat. No. 3,039,869 can also be employed. Such developing agents can be employed in the liquid processing composition or may be contained, at least in part, in any layer or layers of the photographic element or film unit such as the silver halide emulsion layers, the dye image-providing material layers, interlayers, image-receiving layer, etc.

In highly preferred embodiments of this invention, the photographic element or film unit contains a compound in addition to said immobile compounds, which is an antifoggant or development restrainer which substantially prevents any further development of a silver halide emulsion after the initial imagewise development has occurred. Generally, the compound is one which will at least prevent fog buildup in a silver halide layer during the time necessary to release a substantial amount of the photographically useful group from the unoxidized compound. Typical useful development restrainer precursors which can be used to permit initial development but restrain development thereafter are disclosed in U.S. Pat. No. 3,260,597 by Weyerts, U.S. Ser. No. 367,306 by Hammond et al now abandoned, and refiled and issued as U.S. Pat. No. 4,009,029 on Feb. 22, 1977, and the like. Conventional development restrainers can also be used in the photographic elements or film units wherein they are located in the processing composition, in layers adjacent the silver halide emulsion layers, in the receiving element, in a cover sheet, etc., where contact with the silver halide emulsion is delayed until after the initial image-recording development has occurred.

In a photographic element according to the invention, each silver halide emulsion layer containing a dye image-providing material or having the dye image-providing material present in a contiguous layer may be separated from the other silver halide emulsion layers in the negative portion of the film unit by materials in addition to those described above, including gelatin, calcium alginate, or any of those disclosed in U.S. Pat. No. 3,384,483, polymeric materials such as polyvinylamides as disclosed in U.S. Pat. No. 3,421,892, or any of those disclosed in French Pat. No. 2,028,236 or U.S. Pat. Nos. 2,992,104, 3,043,692, 3,044,873, 3,061,428, 3,069,263, 3,069,264, 3,121,011 and 3,427,158.

Generally, except where noted otherwise, the silver halide emulsion layers in the invention comprise photosensitive silver halide dispersed in gelatin and are about 0.6 to 6 microns in thickness; the dye image-providing materials are dispersed in an aqueous alkaline solution-permeable polymeric binder, such as gelatin, in the same layer as the silver halide emulsion or as a separate layer about 1 to 7 microns in thickness; and the alkaline solution-permeable polymeric interlayers, e.g., gelatin, are about 1 to 5 microns in thickness. Of course, these thicknesses are approximate only and can be modified according to the product desired. In addition to gelatin, other suitable hydrophilic materials include both naturally occurring substances such as proteins, cellulose derivatives, polysaccharides such as dextran, gum arabic and the like; and synthetic polymeric substances such as water-soluble polyvinyl compounds like poly(-vinylpyrrolidone), acrylamide polymers and the like.

The photographic emulsion layers and other layers of a photographic element employed in the practice of this invention can also contain, alone or in combination with hydrophilic, water-permeable colloids, other synthetic polymeric compounds such as dispersed vinyl compounds such as in latex form, and particularly those which increase the dimensional stability of the photographic materials. Suitable synthetic polymers include those described, for example, in U.S. Pat. No. 3,142,568 by Nottorf issued July 28, 1964, U.S. Pat. No. 3,193,386 by White issued July 6, 1965, U.S. Pat. No. 3,062,674 by Houck et al issued Nov. 6, 1962, U.S. Pat. No. 3,220,844 by Houck et al issued Nov. 30, 1965, U.S. Pat. No. 3,287,289 by Ream et al issued Nov. 22, 1966, and U.S. Pat. No. 3,411,911 by Dykstra issued Nov. 19, 1968. Particularly effective are water-insoluble polymers of alkyl acrylates and methacrylates, acrylic acid, sulfoalkyl acrylates or methacrylates, those which have cross-linking sites which facilitate hardening or curing, and those having recurring sulfobetaine units as described in Dykstra, Canadian Pat. No. 774,054.

Any material can be employed as the image-receiving layer in the film units of this invention as long as the desired function of mordanting or otherwise fixing the dye images will be obtained. The particular material chosen will, of course, depend upon the dye image to be mordanted as mentioned hereinbefore.

Use of a pH-lowering layer in the film units of the invention will usually increase the stability of the transferred image. Generally, the pH-lowering layer will effect a reduction in the pH of the image layer from about 13 or 14 to at least 11 and preferably 5–8 within a short time after imbibition. For example, polymeric acids as disclosed in U.S. Pat. No. 3,362,819 issued Jan. 9, 1968, U.S. Pat. No. 2,584,030 issued Jan. 29, 1952, or U.S. Pat. No. 2,548,575 issued Apr. 10, 1951, or Belgian Pat. No. 603,747 issued May 31, 1961, p. 47, may be employed. Such polymeric acids reduce the pH of the film unit after development to terminate development and substantially reduce further dye transfer and thus stabilize the dye image. Such polymeric acids comprise polymers containing acid groups, such as carboxylic acid and sulfonic acid groups, which are capable of forming salts with alkali metals, such as sodium or potassium, or with organic bases, particularly quaternary ammonium bases, such as tetramethyl ammonium hydroxide. The polymers can also contain potentially acid-yielding groups such as anhydrides or lactones or other groups which are capable of reacting with bases to capture and retain them. Generally, the most useful polymeric acids contain free carboxyl groups, being insoluble in water in the free acid form and which form water-soluble sodium and/or potassium salts. Examples of such polymeric acids include dibasic acid half-ester derivatives of cellulose, which derivatives contain free carboxyl groups, e.g., cellulose acetate hydrogen phthalate, cellulose acetate hydrogen gluturate, cellulose acetate hydrogen succinate, ethyl cellulose hydrogen succinate, ethyl cellulose acetate hydrogen succinate, cellulose acetate succinate hydrogen phthalate; ether and ester derivatives of cellulose modified with sulfoanhydrides, e.g., with ortho-sulfobenzoic anhydride; polystyrene sulfonic acid; carboxymethyl cellulose; polyvinyl hydrogen phthalate; polyvinyl acetate hydrogen phthalate; polyacrylic acid, acetals of polyvinyl alcohol with carboxy or sulfo-substituted aldehydes, e.g., o-, m- or p-benzaldehyde sulfonic acid or carboxylic acid; partial esters of ethylene/maleic anhydride copolymers; partial esters of methylvinyl ether/maleic anhydride copolymers; etc. In addition, solid monomeric acid materials could also be used such as palmitic acid, oxalic acid, sebacic acid, hydrocinnamic acid, metanilic acid, paratoluenesulfonic acid and benzenedisulfonic acid. Other suitable materials are disclosed in U.S. Pat. Nos. 3,422,075 and 2,635,048.

The pH-lowering layer is usually about 0.3 to about 1.5 mils in thickness and can be located in the receiver portion of the film unit between the support and the image-receiving layer, on the cover sheet, or anywhere within the film unit, as long as the desired function is obtained.

An inert timing or spacer layer coated over the pH-lowering layer may also be used to "time" or control the pH reduction of the film unit as a function of the rate at which the alkali diffuses through the inert spacer layer. Timing layers can also be used effectively to isolate development restrainers in a layer adjacent the image-receiving layer wherein restrainers will be released after alkali breakdown of the timing layer. Examples of such timing layers include gelatin, polyvinyl alcohol or any of those disclosed in U.S. Pat. No. 3,455,686. The timing layer is also effective in evening out the various reaction rates over a wide range of temperatures; e.g., premature pH reduction is prevented when imbibition is effected at temperatures above room temperature, for example, at 95° to 100° F. The timing layer is usually about 0.1 to about 0.7 mil in thickness. Especially good results are obtained when the timing layer comprises a hydrolyzable polymer or a mixture of such polymers which are slowly hydrolyzed by the processing composition. Examples of such hydrolyzable polymers include polyvinyl acetate, polyamides, cellulose esters, etc.

The alkaline processing composition employed in this invention can be conventional aqueous solutions of an alkaline material, e.g., sodium hydroxide, sodium carbonate or an amine such as diethylamine, preferably possessing a pH in excess of 12, and preferably contains a developing agent as described previously. The solution also preferably contains a viscosity-increasing compound such as a high-molecular-weight polymer, e.g., a water-soluble ether inert to alkaline solutions such as hydroxyethyl cellulose or alkali metal salts of carboxymethyl cellulose such as sodium carboxymethyl cellulose. A concentration of viscosity-increasing compound of about 1 to about 5% by weight of the processing solution is preferred which will impart thereto a viscosity of about 100 cps. to about 200,000 cps.

The alkaline processing composition employed in this invention can also contain a desensitizing agent such as methylene blue, nitro-substituted heterocyclic compounds, 4,4'-bipyridinium salts, etc., to insure that the photosensitive element is not further exposed after it is removed from the camera for processing.

While the alkaline processing composition used in this invention can be employed in a rupturable container, as described previously, to facilitate conveniently the introduction of processing composition into the film unit, other means of discharging processing composition within the film unit could also be employed, e.g., interjecting processing solution with communicating members similar to hypodermic syringes which are attached either to a camera or camera cartridge, as described in Harvey, U.S. Pat. No. 3,352,674 issued Nov. 14, 1967.

In certain embodiments of our invention, and especially with integral format film units, an opacifying agent can be employed in the processing composition in our invention. Examples of opacifying agents include carbon black, barium sulfate, zinc oxide, barium stearate, silver flake, silicates, alumina, zirconium oxide, zirconium acetyl acetate, sodium zirconium sulfate, kaolin, mica, titanium dioxide, organic dyes such as indicator dyes, nigrosines, or mixtures thereof in widely varying amounts depending upon the degree of opacity desired. In general, the concentration of opacifying agent should be sufficient to prevent further exposure of the film unit's silver halide emulsion or emulsions by ambient actinic radiation through the layer of processing composition, either by direct exposure through a support or by light piping from the edge of the element. For example, carbon black or titanium dioxide will generally provide sufficient opacity when they are present in the processing solution in an amount of from about 5 to 40% by weight. After the processing solution and opacifying agent have been distributed into the film unit, processing may take place out of the camera in the presence of actinic radiation in view of the fact that the silver halide emulsion or emulsions of the laminate are appropriately protected by incident radiation, at one major surface by the opaque processing composition and at the remaining major surface by the alkaline solution-permeable opaque layer. In certain embodiments, ballasted indicator dyes or dye precursors can be incorporated in a layer on the exposure side of the photosensitive layers; the indicator dye is preferably transparent during exposure and becomes opaque when contacted with the processing composition. Opaque binding tapes can also be used to prevent edge leakage of actinic radiation incident on the silver halide emulsion.

When titanium dioxide or other white pigments are employed as the opacifying agent in the processing composition in our invention, it may also be desirable to employ in cooperative relationship therewith a pH-sensitive opacifying dye such as a phthalein dye. Such dyes are light-absorbing or colored at the pH at which image formation is effected and colorless or not light-absorbing at a lower pH. Other details concerning these opacifying dyes are described in French Pat. No. 2,026,927.

The alkaline solution-permeable, substantially opaque, light-reflective layer in the integral negative receiver film units of our invention can generally comprise any opacifier dispersed in a binder as long as it has the desired properties. Particularly desirable are white light-reflective layers since they would be esthetically pleasing backgrounds on which to view a transferred dye image and would also possess the optical properties desired for reflection of incident radiation. Suitable opacifying agents include titanium dioxide, barium sulfate, zinc oxide, barium stearate, silver flake, silicates, alumina, zironium oxide, zirconium acetyl acetate, sodium zirconium sulfate, kaolin, mica, or mixtures thereof in widely varying amounts depending upon the degree of opacity desired. The opacifying agents may be dispersed in any binder such as an alkaline solution-permeable polymeric matrix such as, for example, gelatin, polyvinyl alcohol, and the like. Brightening agents such as the stilbenes, coumarins, triazines and oxazoles can also be added to the light-reflective layer, if desired. When it is desired to increase the opacifying capacity of the light-reflective layer, dark-colored opacifying agents may be added to it, e.g., carbon black, nigrosine dyes, etc. Another technique to increase the opacifying capacity of the light-reflective layer is to employ a separate opaque layer underneath it comprising, e.g., carbon black, nigrosine dyes, etc., dispersed in an alkaline solution-permeable polymeric matrix such as, for example, gelatin, polyvinyl alcohol, and the like. Such an opaque layer would generally have a density of at least 4 and preferably greater than 7 and would be substantially opaque to actinic radiation. The opaque layer may also be combined with a developer scavenger layer if one is present. The light-reflective and opaque layers are generally 1 to 6 mils in thickness, although they can be varied depending upon the opacifying agent employed, the degree of opacity desired, etc.

The supports of the film elements of this invention can be any material as long as it does not deleteriously affect the photographic properties of layers thereon and is substantially dimensionally stable. Typical useful supports include cellulose nitrate film, cellulose acetate film, poly(vinyl acetal) film, polystyrene film, poly(ethyleneterephthalate) film, polycarbonate film, poly-olefins such as polyethylene and polypropylene film, and related films or resinous materials, as well as glass. In those embodiments where the support is transparent, it is usually about 2 to 6 mils in thickness and may contain an ultraviolet absorber if desired.

The support of the integral negative receiver film assemblies and the cover sheet used with these assemblies of this invention can be any of the materials mentioned above for the support. If desired, an ultraviolet-absorbing material can be employed in the support or cover sheet.

The photosensitive substances used in this invention are preferably silver halide compositions and can comprise silver chloride, silver bromide, silver bromoiodide, silver chlorobromoiodide and the like, or mixtures thereof. The emulsions may be coarse- or fine-grain and can be prepared by any of the well-known procedures, e.g., single-jet emulsions, double-jet emulsions, such as Lippmann emulsions, ammoniacal emulsions, thiocyanate or thioether ripened emulsions such as those described in U.S. Pat. No. 2,222,264 by Nietz et al, U.S. Pat. No. 3,320,069 by Illingsworth, and 3,271,157 by McBride. Surface-image emulsions can be used or internal-image emulsions can be used such as those described in U.S. Pat. No. 2,592,250 by Davey et al, U.S. Pat. No. 3,206,313 by Porter et al, and U.S. Pat. No. 3,447,927 by Bacon et al. The emulsions may be regular-grain emulsions such as the type described in Klein and Moisar, J. Phot. Sci. Vol. 12, No. 5, Sept/Oct., 1964, pp. 242–251. If desired, mixtures of surface- and internal-image emulsions can be used as described in Luckey et al, U.S. Pat. No. 2,996,382.

Negative-type emulsions can be used or direct-positive emulsions can be used such as those described in U.S. Pat. No. 2,184,013 by Leermakers, U.S. Pat. No. 2,541,472 by Kendall et al. U.S. Pat. No. 3,367,778 by Berriman, U.S. Pat. No. 3,501,307 by Illingsworth et al issued Mar. 17, 1970, U.S. Pat. No. 2,563,785 by Ives, U.S. Pat. No. 2,456,953 by Knott et al, U.S. Pat. No. 2,861,885 by Land, U.S. Pat. No. 3,761,276 by Evans, U.S. Pat. No. 3,761,266 by Milton, U.S. Pat. No. 3,736,140 by Collier et al and U.S. Pat. No. 3,730,723 by Gilman et al, British Patent No. 723,019 by Schouwenaars, and U.S. Ser. No. 123,007 by Gilman et al filed Mar. 10, 1971, now U.S. Pat. No. 3,761,267 and Ser. No. 154,155 by Gilman et al filed June 17, 1971, now abandoned and refiled as Ser. No. 398,906 on Sept. 19, 1973.

In still another embodiment, the intramolecular nucleophilic displacement compounds can be coated in a layer in an alkali-permeable binder on a support to provide what is referred to as a receiver element. The receiver element can be processed by positioning it in interfacial contact with a photographic silver halide element in the presence of an alkaline solution and a silver halide developer. In those areas where oxidized developer diffuses to the receiver layer, the nucleophilic displacement compound will be oxidized, and if it contains a dye moiety it will provide a permanent image dye record in the areas corresponding to silver halide development. The remainder of the dye can be removed from the element, for example, by washing, after intramolecular nucleophilic displacement. With proper selection of the image dye-providing moieties, a black-and-white image can be obtained. Also, if the nucleophilic compound contains a tanning agent as the photographically useful moiety, it is possible to obtain a tanned image record in areas where silver halide development does not take place, i.e., a positive image record if a negative emulsion is used.

In this application, certain groups are identified with reference to the periodic table. The reference table is located on pp. 400–1of the *Handbook of Chemistry and Physics*, 39th Ed., Chemical Rubber Publishing Co.

The photographic elements, as described above, generally comprise at least one layer containing photographic recording material, such as silver halide, having associated therewith an immobile compound. The term "associated therewith" is a term of art in the photographic industry and generally refers to said immobile compound in alkaline-permeable relationship with said photographic recording material. The respective materials can be coated in the same layers or separate layers, as long as they are effectively associated and isolated to provide for the desired reactions before a substantial amount of the intermediate reactant products diffuse into adjacent photographic recording layers, etc.

Compounds referred to in the following examples by roman numeral are identified structurally above.

The invention can be further illustrated by the following examples.

EXAMPLE 1:

Compound I described above can be prepared by the following procedure:

(A) 1,4-methano-1,2,3,4-tetrahydro-5,8-naphthoquinone

Concentrated nitric acid is added dropwise to 20.45 g. (0.1165 mole) of 5,8-dihydroxy-1,4-methano-1,2,3,4-tetrahydronaphthalene contained in a flask set in an ice bath. When the evolution of gas is completed, the ice bath is removed and the semisolid mass is stirred at room temperature. The mixture is diluted with ice water and extracted with ether. The ether extract is washed with saturated sodium chloride solution and concentrated to an oil in a rotary evaporator. The oil weighs 19.4 g. (96% yield). The structure is confirmed by NMR and IR analysis.

(B)
1,4-methano-6-octadecylamino-1,2,3,4-tetrahydronaphthoquinone

A portion (6.96 g., 0.04 mole) of the methano-naphthoquinone prepared in (A) above is taken up in 15 ml. of ethanol contained in a flask. Solid octadecylamine (5.38 g., 0.02 mole) is washed into the flask with ethanol. The mixture turns a deep purple almost immediately. After 15 min., the purple crystals that have formed are filtered and dried. The yield is 7.07 g. (80.3%). Thin-layer chromatography (TLC) on silica gel and elution with dichloromethane show an essentially homogeneous material. The NMR and mass spectra are consistent with the required structure.

(C) Compound 1

A portion (5 g., 0.0114 mole) of (B) prepared as described above is reduced to the corresponding 5,8-diol at room temperature in 100 ml. of tetrahydrofuran (THF) with hydrogen (35 p.s.i.) and Pd on carbon as the catalyst. Upon completion of the reduction, the mixture is filtered free from the catalyst directly into a flask containing 1.05 g. (0.0052 mole) of m-nitrophenoxycarbonyl chloride dissolved in 10 ml. THF under nitrogen. The carbonyl chloride/THF solution is stirred during the filtration and for 15 min. thereafter. The reaction mixture is concentrated to a syrup in a rotary evaporator. The concentrate is chromatographed on silica gel with a mixture of dichloromethane and ethyl acetate in a ratio of 19:1. The yield of product is 2.51 g. The NMR and IR spectra are consistent with the structure of Compound I.

EXAMPLE 2:

Compound II described above can be prepared as follows:

(A)
6-(3-aminophenoxycarbonyl-N-octadecylamino)-1,4-methano-1,2,3,4-tetrahydro-5,8-naphthalenediol A 6.72-g. (0.0140-mole quantity of the nitro compound (C) of Example 1 is dissolved in 150 ml. THF and catalytically reduced to the corresponding aniline with hydrogen (50 p.s.i.) and palladium on carbon. TLC (50:50-dichloromethane-ethyl acetate) shows one major component. The reaction mixture is filtered and used without further purification in the next step.

(B) Compound II

To a solution of 7 g. (0.0122 mole) of N-tert-butyl-4-p-chlorosulfonylphenylazo-1-hydroxy-5-methanesulfonamido-2-naphthalenesulfonamide in 100 ml. N,N-dimethylformamide (DMF) are added 1.5 g. (0.0124 mole) of N,N-dimethylaniline followed by the syrup of the amine prepared in step (A) above. The mixture is stirred vigorously for about 1 hr. followed by dilution with 5% HCl and water. The reaction mixture is filtered and extracted with dichloromethane. The extract is washed with saturated sodium chloride solution, dried over $MgSO_4$ and concentrated.

A portion (3.5 g.) of the concentrate is chromatographed on dry column silica gel and eluted with 4:1-methylene chloride-acetone. After a forerun, a pure component is eluted. The IR spectrum is consistent with the structure of the desired dye.

EXAMPLE 3:

Compound II described above can be prepared as follows:

(A)
5,8-diacetoxy-1,4-methano-6-(3-nitrophenoxycarbonyl-N-octadecylamino)-1,2,3,4-tetrahydronaphthalene This compound is prepared from compound (C), Example 1, by conventional acetylation with a mixture of acetic anhydride and sulfuric acid.

(B)
5,8-diacetoxy-1,4-methano-6-(3-aminophenoxycarbonyl-N-octadecylamino)-1,2,3,4-tetrahydronaphthalene This compound is prepared from the compound of step (A) next above by catalytic reduction employing hydrogen and Pd/C.

(C) Compound III

About 2.3 g. (ca. 0.0035 mole) of compound (B) above are dissolved in 40 ml. DMF and 0.5 g. of pyridine is added. Over a period of 5 min., 2.2 g. (0.0038 mole) of N-tert-butyl-4-p-chlorosulfonylphenylazo-1-hydroxy-5-methanesulfonamido-2-naphthalenesulfonamide dissolved in DMF are added to the mixture of compound (B) and pyridine. After standing 1 hr., the reaction mixture is diluted with 5% HCl and extracted with methylene chloride. The extract is dried and concentrated and purified by column chromatography on silica gel. The NMR and IR spectra are consistent with the structure of Compound III.

EXAMPLE 4:

Compound IV described above can be prepared as follows:

(A)
1,4-methano-6-methyl-1,2,3,4-tetrahydronaphthoquinone

Step 1. A mixture of 122.12 g. (1.0 mole) of methylbenzoquinone and 150 ml. benzene, contained in a flask fitted with a dry-ice condenser, is well-cooled in an ice-methanol bath and 132.2 g. (2.0 moles) of cyclopentadiene are added. The resulting exothermic reaction subsides after 1–2 min. The mixture is stirred for 35–40 min. and concentrated to dryness in a rotary evaporator. The residue crystallizes on cooling and is used without further treatment in the next step. The NMR and infrared spectra are consistent with the desired structure.

Step 2. One mole (188.22 g.) of the crude product of Step 1 is refluxed for 6 days in 400 ml. of ethanol with 50 g. of neutral alumina. The reaction mixture is concentrated to a dark oil which is triturated with hexane and glacial acetic acid and allowed to crystallize. The crystals are filtered and dried to yield 78.3 g. of 1,4-methano-6-methyl-1,2-dihydronaphthalene-5,8-diol. A second portion of 77.8 g. is obtained by refluxing the filtrate with fresh neutral alumina for 4 days. The NMR and infrared spectra are consistent with the desired structure.

Step 3. A quantity of 82.3 g. (0.437 mole) of Step 2 is mixed with 500 ml. ethanol and hydrogenated for about 30 min. in a Parr Shaker over 10% palladium on carbon. The reaction mixture is filtered through celite and concentrated to a dark syrup which slowly crystallizes on standing. This material is used without further treatment in the next step. The structure is confirmed by both infrared and NMR spectra.

Step 4. The crude product from Step 3 is oxidized with nitric acid in the conventional manner. The reaction mixture is poured into ice water and extracted with dichloromethane. The extract is dried and concentrated. The resulting syrup is chromatographed on Florisil with dichloromethane. The eluant is concentrated to a yellow syrup which is the desired naphthoquinone. TLC indicates a small amount of impurity. The NMR and infrared spectra are consistent with the desired structure.

(B)
6-methyl-7-n-octadecylamino-1,4-methano-1,2,3,4-tetrahydro-5,8-naphthoquinone A mixture of 75.0 g. (0.398 mole) of crude 1,4-methano-6-methyl-1,2,3,4-tetrahydro-1,4-naphthoquinone, 53.6 g. (0.199 mole) of n-octadecylamine and 500 ml. of ethanol is warmed to about 65° C. The reaction is monitored by TLC. After about 2-½ hr., the reaction mixture is cooled in ice water and concentrated. The concentrate is chromatographed on Florisil with dichloromethane. The crude purple eluate (61.7 g.) is taken up in 200 ml. ethanol and cooled in an ice bath to precipitate the product. The precipitate is redissolved in ethanol and the mixture is cooled to precipitate the product. A first crop of 31 g. of the desired compound is obtained as a low-melting solid. The mass spectrum UV/visible and infrared spectra are consistent with the expected structure.

(C)
1,4-methano-6-methyl-7-(3-nitrophenoxycarbonyl-N-octadecylamino)-1,2,3,4-tetrahydro-5,8-naphthalenediol A 31.0-g. quantity (0.068 mole) of compound (B) above is reduced in 200 ml. of tetrahydrofuran to the corresponding naphthalenediol by the procedure of Example 1, part (C). The hydrogenation mixture is filtered through celite under $N_2$ into a flask containing 6.83 g. (0.034 mole) of m-nitrophenyl chloroformate dissolved in dry THF. After stirring for 1½ hr., the reaction mixture is acidified with gaseous hydrogen chloride and concentrated to a dark syrup in a rotary evaporator at a bath temperature under 35° C. The concentrate is chromatographed on silica gel with a 19:1 mixture of dichloromethane and ethyl acetate. The total amount of the first crop of product is 10.33 g. The structure is confirmed by IR.

Upon mass spectral analysis, (C) thermally cyclizes and gives the parent ions of m-nitrophenol and the cyclization product, thus confirming the structure.

The structure of (C) is further supported by oxidation with nitric acid to a quinone derivative which has appropriate infrared and mass spectra.

(D) Compound IV

The nitro group in compound (C) is reduced to an amino group according to the method of Example 2, compound (A). When the reduction is completed, the reaction mixture is filtered through celite and concentrated to a smaller volume. The concentrate is dissolved in DMF and added all at once to a solution of 6.00 g. (0.00964 mole) of 3-(4-benzoyloxy-3-cyanophenylazo)-benzenesulfonyl chloride and 1.2 g. (0.01 mole) of N,N-dimethylaniline in DMF. The reaction mixture is stirred for 1¼ hr. and then poured over a mixture of ice, water and 5% HCl. The resulting slurry is stirred well and filtered and the solid is dried in a vacuum oven.

The crude product is chromatographed on silica gel with a 19:1 mixture of dichloromethane and ethyl acetate. The fractions containing the desired product (as shown by TLC) are combined and concentrated to an orange oil which is triturated with hexane to induce crystallization. The crystals are filtered, washed with hexane and dried. The yield is 4.9 g. The IR spectrum and NMR are consistent with the structure of Compound IV.

EXAMPLE 5

Compound V described above can be prepared as follows:

A quantity (4.0 g., 0.00643 mole) of compound (C) in Example 4 is prepared as described in that example, and the nitro group is converted to an amino group by catalytic reduction according to the procedure of Example 2, compound (A). The reaction mixture is filtered and concentrated to dryness in a rotary evaporator at a pot temperature of 30°-35° C.

To a solution of 4.9 g. of 3-[5-(p-chlorobenzoyloxy)-8-(4-nitro-3-methylsulfonylphenylazo)-1-naphthyl-sulfamoyl]benzenesulfonyl chloride in 30 ml. DMF is added 0.95 g. N,N-dimethylaniline. A solution of the concentrated amino compound, prepared above, in DMF is added all at once with stirring. The reaction mixture is stirred for 1 hr. and then poured with stirring onto a mixture of ice, water and 5% HCl. The resulting slurry is stirred for 30 min. and filtered. The collected solid is washed with water and dried.

The crude product (9.15 g.) is chromatographed on silica gel with a 50:50 mixture of dichloromethane and ethyl acetate. The portions of eluate containing the desired product (as determined by TLC) are combined, concentrated and rechromatographed on silica gel with a 9:1 mixture of THF and benzene. The portions of eluate containing the product are combined and concentrated to dryness. The residue is dissolved in a minimum of ethyl acetate, cooled and filtered. The collected product (2.67 g.) is dried in a vacuum over for 16 hr. The IR spectrum is consistent with the expected structure. Infrared absorptions: 2960 and 2870 $cm^{-1}$; carbonyl absorptions are present but not resolved.

EXAMPLE 6:

Compound VI described above can be prepared as follows:

A quantity (4.25 g., 0.00683 mole) of compound (C) in Example 4 is prepared as described in that example, and the nitro group is converted to an amino group by catalytic reduction according to the procedure of Example 2, compound (A). The reaction mixture is filtered through celite and concentrated to a syrup in a rotary evaporator.

To a solution of 3.68 g. (0.00717 mole) of 3-(4-ethoxycarbonyloxy-8-methylsulfonamido-1-naphthylazo)-benzenesulfonyl chloride in 30 ml. DMF is added 0.90 g. (0.00751 mole) of N,N-dimethylaniline. A solution of the concentrated amino compound, prepared above, in THF is added all at once. The reaction mixture is stirred at room temperature for 45 min. and then poured into a mixture of ice, water and 5% HCl. The resulting slurry is stirred for 30 min. and filtered. The filter cake is dried in a vacuum oven.

The crude product (6.83 g.) is chromatographed on silica gel with an 85:15 mixture of $CH_2Cl_2$ and ethyl acetate. The portions of eluate that contain product (TLC analysis) are combined and concentrated. Trituration of the concentrate with hexane induces solidification and crystallization of product. The crystals are filtered and dried. The yield is 3.2 g. The IR spectrum is consistent with the expected structure.

EXAMPLE 7:

A photographic element for image-transfer film units is prepared by coating layers on a support as follows:

Layer 1: polyethylene terephthalate film support

Layer 2: layer containing a negative silver bromide emulsion (0.8 micron mean grain size) at 100 mg. Ag/ft.$^2$, gelatin at 150 mg./ft.$^2$ and Compound I at 77 mg./ft.$^2$ dissolved in diethyl lauramide at 77 mg./ft.$^2$ Layer 3: layer containing gelatin at 50 mg./ft.$^2$ The photographic element is exposed through a graduated-density test object for 1/100 sec. on a 1B sensitometer. The exposed element is then laminated with a receiver sheet having a layer thereon containing copoly(styrene--co-tri-hexyl-p-vinylbenzylammonium chloride) as described in Cohen et al, U.S. Ser. No. 400,778 filed Sept. 26, 1973, and a processing solution, containing 10 g. KOH, 3 g. 4-hydroxymethyl-4-methyl-1-phenyl-3-pyrazolidone, 40 g. of carboxymethyl cellulose and water to provide a liter of fluid, is spread between the receiver sheet and the photographic element. The receiver sheet is separated from the photographic element after processing for 1 min. and the receiver sheet contains a positive yellow-dye image of the photographed test object with a maximum density of 0.52 and a minimum density of 0.22.

EXAMPLE 8:

A photographic element is prepared as described in Example 7, except Compound II is used in layer 2 at 34 mg./ft.$^2$ instead of Compound I. The element is exposed as in Example 7 and is processed for 20 min. in contact with the receiver element of Example 7 after application of a processing composition with the following ingredients: 5 g. KOH, 10 g. KBr, 3 g. 4-hydroxymethyl-4-methyl-1-phenyl-3-pyrazolidone, 40 g. carboxymethyl cellulose and the balance of water to provide 1 liter of fluid.

After processing, the receiver element contains a positive dye image of the photographed test object. The maximum density is 1.6 and the minimum density is 0.4.

EXAMPLE 9:

A photographic element is prepared as described in Example 7, except Compound II is used in layer 2 at a coverage of 36 mg./ft.$^2$ instead of Compound I. The element is exposed as in Example 7 and is processed for 20 min. in contact with the receiver element of Example 7 after application of a processing composition prepared with the following ingredients: 100 g. KOH, 3 g. 4-hydroxy-4-methyl-1-phenyl-3-pyrazolidone, 1.5 g. of 5-methylbenzotriazole, 40 g. carboxymethyl cellulose and the balance of water to provide 1 liter of fluid.

Upon separation of the receiver element from the photographic element, a positive image record is present in the receiver sheet.

EXAMPLE 10:

A photographic element for use in an image-transfer film unit is prepared by coating layers on a support as follows:

Layer 1: transparent polyethylene terephthalene film support

Layer 2: layer containing a negative silver halide emulsion at 150 mg. Ag/ft.$^2$, gelatin at 370 mg./ft.$^2$, 4-hydroxymethyl-1-phenyl-3-pyrazolidone at 5 mg./ft.2, 5-(2-cyanoethylthio)-1-phenyltetrazole at 10 mg./ft.$^2$ dissolved in tricresyl phosphate at 30 mg./ft.$^2$, and Compound IV at 137 mg./ft.$^2$ dissolved in diethyl lauramide at 137 mg./ft.$^2$ Layer 3: layer containing gelatin at 175 mg./ft.$^2$, 2,5-di-sec-dodecylhydroquinone at 70 mg./ft.$^2$ and a yellow filter dye Layer 4: layer containing a negative green-sensitive silver halide emulsion at 150 mg./ft.$^2$, gelatin at 300 mg./ft.$^2$, 4-hydroxymethyl-1-phenyl-3-pyrazolidone at 5 mg./ft.$^2$, 5-(2-cyanoethylthio)-1-phenyltetrazole at 10 mg./ft.$^2$ dissolved in tricresyl phosphate at 30 mg./ft.$^2$, and Compound V at 90 mg./ft.$^2$ dissolved in diethyl lauramide at 90 mg./ft.$^2$ Layer 5: layer containing gelatin at 125 mg./ft.$^2$, 2,5-di-sec-dodecylhydroquinone at 70 mg./ft.$^2$ and a magenta filter dye Layer 6: layer containing red-sensitive negative silver halide emulsion at 150 mg. Ag/ft.$^2$, gelatin at 330 mg./ft.$^2$, 4-hydroxymethyl-5-methyl-1-phenyl-3-pyrazolidone at 5 mg./ft.$^2$, 5-(2-cyanoethylthio)-1-phenyltetrazole at 10 mg./ft.$^2$ dissolved in tricresyl phosphate at 30 mg./ft.$^2$, and Compound VI at 110 mg./ft.$^2$ dissolved in diethyl lauramide at 110 mg./ft.$^2$ Layer 7: layer containing hardened gelatin at 50 mg./ft.$^2$ and bis-vinylsulfonyl methyl ether at 14 mg./ft.$^2$ The photographic element is exposed through the transparent support for 1/50 sec. in a 1B sensitometer through a graduated-density test object selectively through a blue, green, red, yellow, magenta and cyan filter. The sample is laminated with a receiver element as described in Example 7 after application of a processing composition which contains 30 g. KOH, 12 g. 4-hydroxy-5-methyl-1-phenyl-3-pyrazolidone and 40 g. of carboxymethyl cellulose/liter of water.

The receiver sheet is separated from the photographic element after 8 min. of processing. The receiver sheet contains a positive multicolor reproduction of the photographed test object.

EXAMPLE 11:

Compound XII as described above can be prepared by the following procedure:

A. Preparation of 3-dodecyl-6-hydroxy-5,7,8-trimethyl-4H-1,3-benzoxazine

A mixture of paraformaldehyde (6.0 g., 0.2 mole) and dodecylamine (18.5 g., 0.1 mole) is refluxed in ethanol until nearly everything dissolves. A solution of 15.2 g. (0.1 mole) trimethylhydroquinone in 100 ml. of ethanol is added and is refluxed for 2 hr. On cooling, the product precipitates as a fluffy white solid. The yield is 19.3 g. The NMR spectrum confirms the structure.

B. Preparation of 2-dodecylaminoethyl-3,5,6-trimethyl-p-benzoquinone hydrochloride To a stirred solution of 7.24 g. (.02 mole) of oxazine from Section A above in 100 ml. of chloroform are added 7.2 g. N-chlorobenzotriazole. After 30 min. at room temperature, the mixture is washed with 2 N HCl and the organic layer is separated and concentrated. The infrared spectrum of the product shows carbonyl absorption and the mass spectrum indicates the presence of the desired material and some unreacted starting material.

C. Preparation of 2-dodecylamino-3,5,6-trimethylhydroquinone hydrochloride

The product from Section B above is suspended in 75 ml. cold methanol and reduced with excess sodium borohydride. The solution is acidified with 2 N HCl and the white crystalline precipitate is collected. The infrared spectrum indicates the absence of carbonyl absorption.

D. An azo dye having a chloroformate group is prepared as follows:

To a solution of 25.6 g. (.05 mole) of 3-(4-ethoxycarbonyloxy-8-methylsulfonamido-1-naphthylazo)benzenesulfonyl chloride in tetrahydrofuran are added 10.91 g. (0.1 mole) m-aminophenol and 9.10 g. (.015 mole) N,N-dimethyl-aniline. After stirring for 30 min. at room temperature, the solution is concentrated and poured over a mixture of ice and dilute HCl. The crude product is filtered, dried and purified by silica gel chromatography. The yield of crystalline dye is 24.80 g.

To a solution of phosgene in dichloromethane are added 5.85 g. (.01 mole) of the dye from the process next above. A total of 3 equivalents (3.62 g.) of N,N-dimethyl-aniline is added portionwise. The reaction mixture is concentrated to dryness under reduced pressure and used without further purification.

Compound XII is made by adding the chloroformate (.01 mole) of Section D and 6.45 g. of diisopropylethylamine to a solution of 5.15 g. of the amine hydrochloride from Section C above.

After stirring for 20 min. at room temperature, the reaction mixture is quenched with dilute hydrochloric acid and extracted with dichloromethane.

After purification by silica gel chromatography, 0.9 g. of the dye releaser is obtained.

EXAMPLE 12:

A photographic element for image-transfer film units is prepared by coating layers on a support as follows:

Layer 1: polyethylene terephthalate film support

Layer 2: layer containing a negative silver bromide emulsion (0.8 micron mean grain size) at 100 mg. Ag/ft.$^2$, gelatin at 150 mg./ft.$^2$, and Compound XI at 34 mg./ft.$^2$ dissolved in diethyl lauramide at 34 mg./ft.$^2$ Layer 3: layer containing gelatin at 50 mg./ft.$^2$ The photographic element is exposed as described in Example 7 and then laminated with a receiver sheet as described in Example 7 after application of a layer processing composition (0.0015 inch thick) having the composition of KOH at 100 g./l., KBr at 20 g./l., 4-hydroxy-4-methyl-1-phenyl-3-pyrazolidone at 3 g./l., carboxymethylcellulose at 40 g./l. and water to 1 liter. After 10 min. the receiver sheet is separated from the photographic element; the receiver sheet contains a well-defined image record of the test object.

Although the invention has been described in considerable detail with particular reference to certain preferred embodiments thereof, variations and modifications can be effected within the spirit and scope of the invention.

We claim:

1. A compound according to the formula:

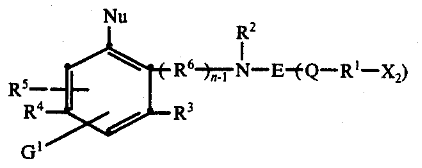

wherein Nu is an oxidizable nucleophilic group or a precursor therefor; E is carbonyl or thiocarbonyl; Q is a bivalent group providing a mono atom linkage between E and $R^1$ and is an amino group providing a mono atom nitrogen linkage, an oxygen atom, a sulfur atom or a selenium atom; $G^1$ is a substituent as defined for Nu or a dialkylamino group; $R^6$ is a bivalent alkylene group or a substituted alkylene group containing from 1-3 atoms in the bivalent linkage; *n* is a positive integer of 1 or 2; $R^1$ is an aromatic group containing from 6-20 carbon atoms or an alkylene group or a substituted alkylene group containing 1-12 carbon atoms; $R^2$ is an alkyl group, a cycloalkyl group or a substituted alkyl group containing from 1-40 carbon atoms, an aryl group or a substituted aryl group containing from 6-20 carbon atoms, or the substituent $X^1$; $R^3$, $R^4$ and $R^5$ are each a mono atom group which is a hydrogen atom or a halogen atom, a polyatomic group which is an alkyl group, a cycloalkyl group, a substituted alkyl group, an aryl group, a substituted aryl group, or a sulfamyl group, the substituent $X^1$ or a 5- to 7-membered cyclic group formed with Nu and $R^5$ or $G^1$ and $R^4$ or $R^3$, and the substituents for $R^3$ and $R^5$ or $R^4$ and $R^5$ when on adjacent positions on the ring may be taken together to form a 5- or 6-membered ring with the carbon atoms to which they are attached, with the provision that, when $R^1$ is an alkylene group or a substituted alkylene group, $R^3$ and $R^4$ are polyatomic groups, and when $G^1$ is a substituent defined for Nu, an adjacent $R^3$ or $R^4$ can be the group:

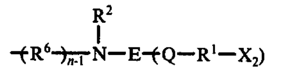

$X^1$ is provided in at least one of $R^2$, $R^3$, $R^4$ or $R^5$ and is a ballasting group or an azo dye moiety, provided one of $X^1$ or $(Q—R^1—X_2)$ is an azo dye moiety, and one of $X^1$ and $(Q—R^1—X_2)$ is a ballasting group which contains at least 8 carbon atoms and is of a size sufficient to render said compound immobile in an alkali-permeable layer of a photographic element.

2. A compound according to claim 1 wherein $(Q—R^1—X_2)$ is said azo dye moiety.

3. A compound according to claim 1 wherein Nu is an hydroxy group.

4. A compound according to claim 1 wherein Nu is an hydroxy group or an alkali-labile precursor therefor.

5. A compound according to claim 1 wherein $R^1$ is a carbocyclic aromatic group.

6. A compound according to claim 1 wherein Nu and $G^1$ are hydroxy groups or hydrolyzable precursors therefor.

7. A compound according to claim 1 wherein $R^2$ is an alkyl group or a substituted alkyl group containing from 8-40 carbon atoms.

8. A compound according to claim 1 wherein Q is an amino group which is monosubstituted with a hydrogen atom or an alkyl group containing from 1-10 carbon atoms.

9. A compound according to claim 1 wherein *n* is 2 and $R^6$ is an alkylene group containing 1 carbon atom.

10. A compound according to claim 1 wherein $G^1$ is para to Nu and $R^4$ and $R^5$ are taken together to form a 5- or 6-membered ring with the carbon atoms to which they are attached.

11. A compound according to claim 1 wherein $(Q—R^1—X_2)$ is an azo dye moiety, Q is an oxygen atom, $G^1$ is an hydroxy group; *n* is 2; $R^6$ is an alkylene group containing 1 carbon atom, and $X^1$ is said ballasting group.

12. A compound according to claim 11 wherein $R^1$ is an aromatic group containing from 6-20 carbon atoms.

13. A compound according to the formula:

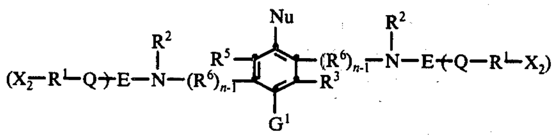

wherein Nu is an oxidizable nucleophilic group or a precursor therefor; E is carbonyl or thiocarbonyl; Q is a bivalent group providing a mono atom linkage between E and $R^1$ and is an amino group providing a mono atom nitrogen linkage, an oxygen atom, a sulfur atom or a selenium atom; $G^1$ is a substituent as defined for Nu; $R^6$ is a bivalent alkylene group or a substituted alkylene group containing from 1-3 atoms in the bivalent linkage; *n* is a positive integer of 1 or 2; $R^1$ is an aromatic group containing from 6-20 carbon atoms, an alkylene group or a substituted alkylene group containing 1-12 carbon atoms; $R^2$ is an alkyl group, a cycloalkyl group or a substituted alkyl group containing from 1-40 carbon atoms, an aryl group or a substituted aryl group containing from 6-20 carbon atoms, or the substituent $X^1$; $R^3$ and $R^5$ are each a mono atom group which is a hydrogen atom or a halogen atom, a polyatomic group which is an alkyl group, a cycloalkyl group, a substituted alkyl group, an aryl group, a substituted aryl group, or a sulfamyl group, the substituent $X^1$ or a 5- to 7-membered cyclic group formed with Nu and $R^5$ or $G^1$ and $R^3$, with the provision that, when $R^1$ is an alkylene group or substituted alkylene group, $R^3$ and $R^5$ are polyatomic groups; and $X^1$ is provided in at least one of $R^2$, $R^3$ or $R^5$ and is a ballast group containing at least 8 carbon atoms and is of a size sufficient to render said compound immobile in an alkali-permeable layer of a photographic element, and each $(Q—R^1—X_2)$ is an azo dye moiety.

14. A compound according to claim 13 wherein Nu and $G^1$ are hydroxy groups or alkali-labile precursors therefor.

15. A compound according to claim 13 wherein Nu and $G^1$ are hydroxy groups.

16. A compound according to claim 13 wherein *n* is 1.

17. A compound according to claim 13 wherein *n* is 2 and $R^6$ is an alkylene group containing 1 carbon atom.

18. A compound according to claim 13 wherein Nu and $G^1$ are hydroxy or a precursor therefor, E is carbonyl and Q is an oxygen atom.

19. A compound according to claim 13 wherein *n* is 2, $R^6$ is a methylene group and $R^2$ is said ballast group.

20. A compound according to the formula:

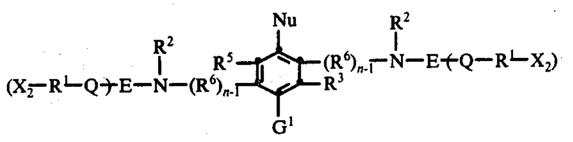

wherein Nu is an oxidizable nucleophilic group or a precursor therefor; E is carbonyl or thiocarbonyl; Q is a bivalent group providing a mono atom linkage between E and $R^1$ and is an amino group providing a mono atom nitrogen linkage, an oxygen atom, a sulfur atom or a selenium atom; $G^1$ is a substituent as defined for Nu; $R^6$ is a bivalent alkylene group or a substituted alkylene group containing from 1-3 atoms in the bivalent linkage; *n* is a positive integer of 1 or 2; $R^1$ is an aromatic group containing from 6-20 carbon atoms, an alkylene group or a substituted alkylene group containing 1-12 carbon atoms; $R^2$ is an alkyl group, a cycloalkyl group or a substituted alkyl group containing from 1-40 carbon atoms, an aryl group or a substituted aryl group containing from 6-20 carbon atoms, or the substituent $X^1$; $R^3$ and $R^5$ are each a mono atom group which is a hydrogen atom or a halogen atom, a polyatomic group which is an alkyl group, a cycloalkyl group, a substituted alkyl group, an aryl group, a substituted aryl group, or a sulfamyl group, the substituent $X^1$ or a 5- to 7-membered cyclic group formed with Nu and $R^5$ or $G^1$ and $R^3$, with the provision that, when $R^1$ is an alkylene group or substituted alkylene group, $R^3$ and $R^5$ are polyatomic groups; and $X^1$ is provided in at least one of $R^2$, $R^3$ or $R^5$ and is a ballast group containing at least 8 carbon atoms and is of a size sufficient to render said compound immobile in an alkali-permeable layer of a photographic element, and each $-(Q-R^1-X_2)$ is a carbocyclic monoazo dye moiety.

21. A compound according to claim 20 wherein Nu and $G^1$ are hydroxy groups or alkali-labile precursors therefor.

22. A compound according to claim 20 wherein Nu and $G^1$ are hydroxy groups.

23. A compound according to claim 20 wherein *n* is 1, $R^1$ is an alkylene group and $R^2$ is an alkyl group.

24. A compound according to claim 20 wherein *n* is 2 and $R^6$ is an alkylene group containing 1 carbon atom.

25. A compound according to claim 20 wherein Nu and $G^1$ are hydroxy or a precursor therefor, E is carbonyl and Q is an oxygen atom.

26. A compound according to claim 20 wherein *n* is 1 and $R^2$ is said ballast group.

27. A compound according to the formula:

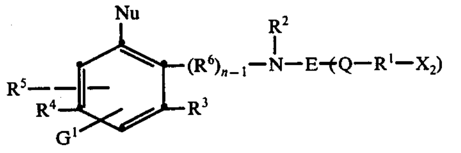

wherein Nu is an oxidizable nucleophilic group or a precursor therefor; E is carbonyl or thiocarbonyl; Q is a bivalent group providing a mono atom linkage between E and $R^1$ and is an amino group providing a mono atom nitrogen linkage, an oxygen atom, a sulfur atom or a selenium atom; $G^1$ is a substituent as defined for Nu or a dialkylamino group; $R^6$ is a bivalent group or substituted alkylene group containing from 1-3 atoms in the bivalent linkage; *n* is a positive integer of 1 or 2; $R^1$ is an aromatic group containing from 6-20 carbon atoms, an alkylene group or substituted alkylene group containing 1-12 carbon atoms; $R^2$ is an alkyl group, a substituted alkyl group or a cycloalkyl group containing from 1-40 carbon atoms, an aryl group or substituted aryl group containing from 6-20 carbon atoms, or the substituent $X^1$; $R^3$, $R^4$ and $R^5$ are each a mono atom group which is a hydrogen atom or a halogen atom, a polyatomic group which is an alkyl group, a cycloalkyl group, a substituted alkyl group, an aryl group, a substituted aryl group, or a sulfamyl group, the substituent $X^1$ or a 5- to 7-membered cyclic group formed with Nu and $R^5$ or $G^1$ and $R^4$ or $R^3$, and the substituents for $R^3$ and $R^5$ or $R_4$ and $R^5$ when on adjacent positions on the ring may be taken together to form a 5- or 6-membered ring with the carbon atoms to which they are attached, with the provision that, when $R^1$ is an alkylene group or substituted alkylene group, $R^3$ and $R^4$ are polyatomic groups, and when $G^1$ is a substituent defined for Nu, an adjacent $R^3$ or $R^4$ can be the group:

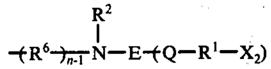

$X^1$ is provided in at least one of $R^2$, $R^3$, $R^4$ or $R^5$ and is a ballasting group or a carbocyclic monoazo dye moiety, provided one of $X^1$ or $-(Q-R^1-X_2)$ is a carbocyclic monoazo dye moiety, and one of $X^1$ and $-(Q-R^1-X_2)$ is a ballasting group which contains at least 8 carbon atoms and is of a size sufficient to render said compound immobile in an alkali-permeable layer of a photographic element.

28. A compound according to claim 27 wherein $(Q-R^1-X_2)$ is said carbocyclic monoazo dye moiety.

29. A compound according to claim 27 wherein Nu is an hydroxy group.

30. A compound according to claim 27 wherein Nu is an hydroxy group or an alkali-labile precursor therefor.

31. A compound according to claim 27 wherein $R^1$ is a carbocyclic aromatic group.

32. A compound according to claim 27 wherein Nu and $G^1$ are hydroxy groups or hydrolyzable precursors therefor.

33. A compound according to claim 27 wherein $R^2$ is an alkyl group or substituted alkyl group containing from 8-40 carbon atoms.

34. A compound according to claim 27 wherein Q is an amino group which is monosubstituted with a hydrogen atom or an alkyl group containing from 1-10 carbon atoms.

35. A compound according to claim 27 wherein *n* is 2 and $R^6$ is an alkylene group containing 1 carbon atom.

36. A compound according to the formula:

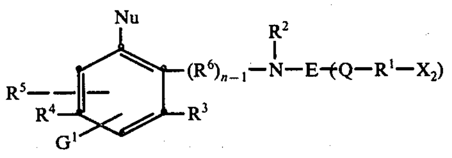

wherein Nu is an oxidizable nucleophilic group or a precursor therefor; E is carbonyl or thiocarbonyl; Q is a bivalent group providing a mono atom linkage between E and $R^1$ and is an amino group providing a mono atom nitrogen linkage, an oxygen atom, a sulfur atom or a selenium atom; $G^1$ is a substituent as defined for Nu or a dialkylamino group; $R^6$ is a bivalent alkylene group or substituted alkylene group containing from 1-3 atoms in the bivalent linkage; *n* is a positive integer of 1 or 2; $R^1$ is an aromatic group containing from 6-20 carbon atoms or an alkylene group or substituted alkylene group containing 1-12 carbon atoms; $R^2$ is an alkyl group, a cycloalkyl group or substituted alkyl group containing from 1-40 carbon atoms, an aryl group or substituted aryl group containing from 6-20 carbon atoms, or the substituent $X^1$; $R^3$, $R^4$ and $R^5$ are each a mono atom group which is a hydrogen atom or a halogen atom, a polyatomic group which is an alkyl group, a cycloalkyl group, a substituted alkyl group, an aryl group, a substituted aryl group, or a sulfamyl group, the substituent $X^1$ or a 5- to 7-membered cyclic group formed with Nu and $R^5$ or $G^1$ and $R^4$ or $R^3$, and the substituents for $R^3$ and $R^5$ or $R^4$ and $R^5$ when on adjacent positions on the ring may be taken together to form a 5- or 6-membered ring with the carbon atoms to which they are attached, with the provision that, when $R^1$ is an alkylene group or substituted alkylene group, $R^3$ and $R^4$ are polyatomic groups; $X^1$ is provided in at least one of $R^2$, $R^3$, $R^4$ or $R^5$ and is a ballasting group which contains at least 8 carbon atoms and is of a size sufficient to render said compound immobile in an alkali-permeable layer of a photographic element; and ($Q-R^1-X_2$) is a carbocyclic monoazo dye moiety.

37. A compound according to claim 36 wherein Q is an oxygen atom and $R^1$ is said aromatic group.

38. A compound according to claim 36 wherein *n* is 2 and $R^6$ is a methylene linkage.

39. A compound according to claim 36 wherein Nu is an hydroxy group or a hydrolyzable precursor therefor and Q is an oxygen atom.

40. A compound according to claim 36 wherein *n* is 2, $R^6$ is a methylene group, Nu is an hydroxy group or a hydrolyzable precursor therefor, $R^1$ is said aromatic group and Q is said oxygen atom.

41. A compound according to claim 36 wherein Q is an oxygen atom, E is carbonyl, Nu is an hydroxy group or a hydrolyzable precursor therefor, $R^6$ is a methylene group and *n* is 2.

42. A compound according to claim 36 wherein *n* is 2, $R^6$ is a methylene group and $R^2$ is said ballast group.

43. A compound according to claim 1 having the formula:

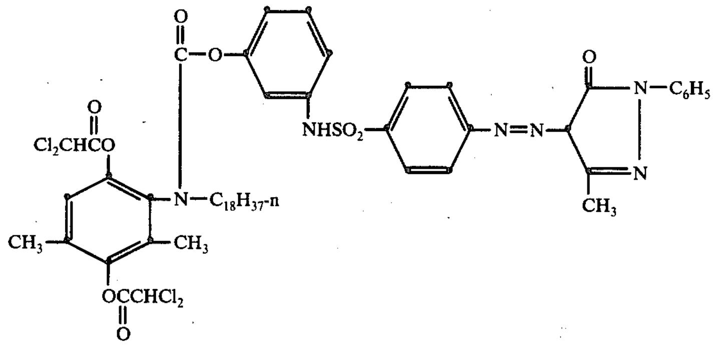

44. A compound having the formula:

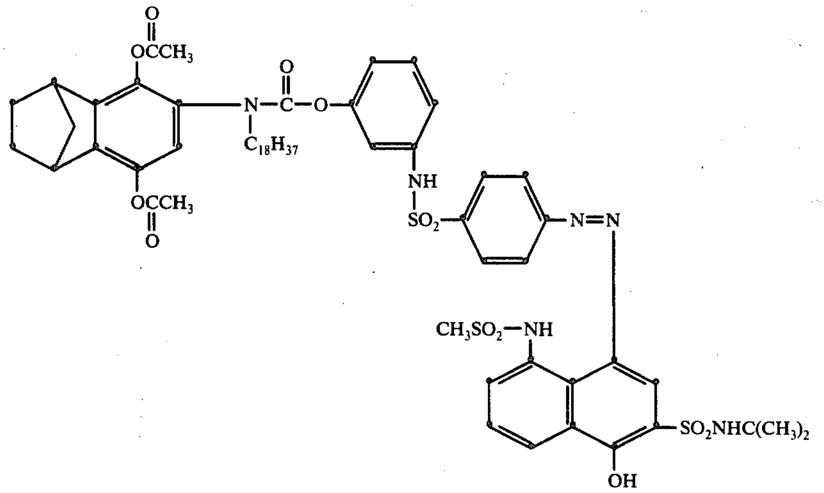

45. A compound having the formula:

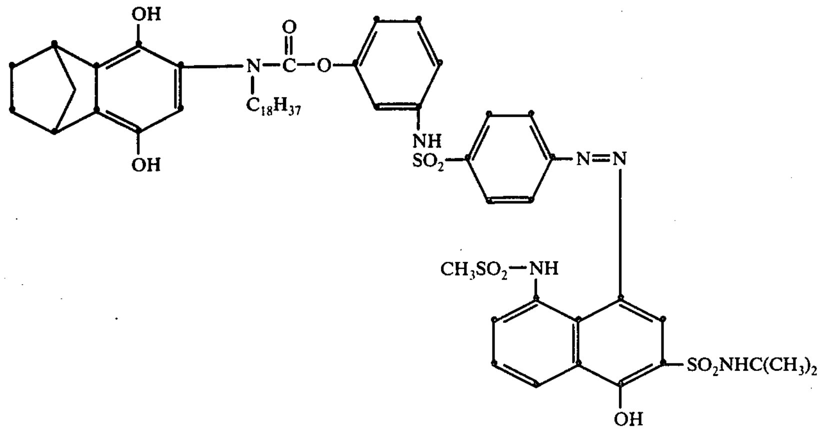
46. A compound having the formula:
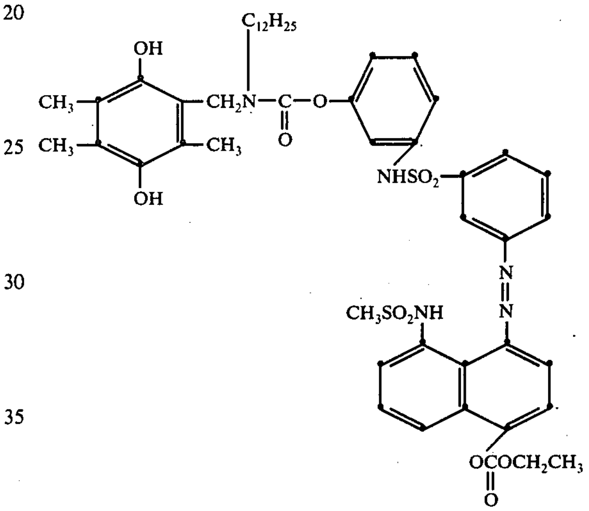
47. A compound having the formula:
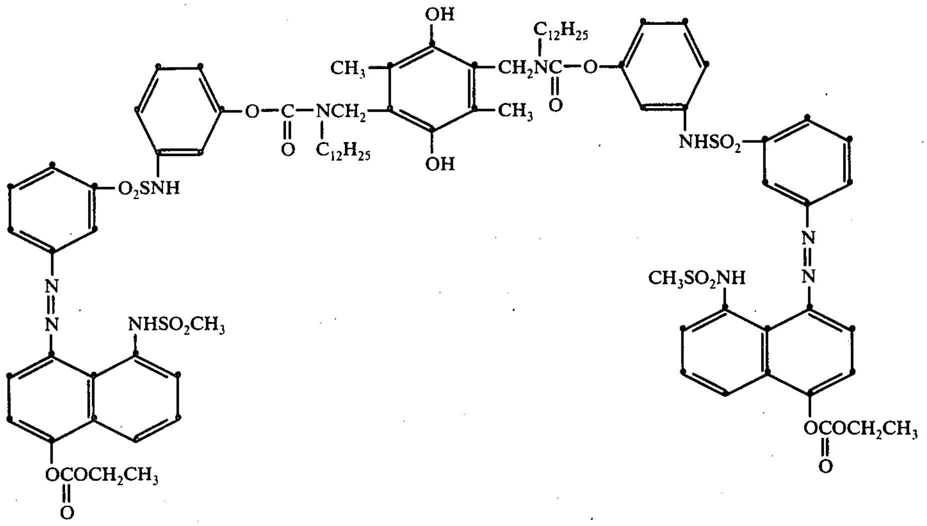
* * * * *

UNITED STATES PATENT AND TRADEMARK OFFICE
CERTIFICATE OF CORRECTION

PATENT NO. : 4,108,850

DATED : August 22, 1978

INVENTOR(S) : Fields et al

It is certified that error appears in the above-identified patent and that said Letters Patent are hereby corrected as shown below:

Title page, item [62], line 2, "3,980,499" should read --3,980,479--. Column 8, line 1, "linkage" should read --linking--. Column 10, line 49, "hydroxylamine" should read --hydroxylamino--. Column 12, last line, "Compound IV " Should be deleted and placed at the head of column 13. Column 13, last formula, that part of the formula reading:

$OC(=O)OOCH_2CH_3$ should read $OC(=O)OCH_2CH_3$ ;

last line, "Compound VII " should be deleted and placed at the head of column 15. Column 19, line 50, "DielsAlder" should read --Diels-Alder--. Column 22, line 63, "redsensitive" should read --red-sensitive--. Column 24, line 62, "(-" after "poly" should be deleted and --(-- placed at the beginning of line 63. Column 30, line 59, "II" should read --III--. Column 33, line 35, "over" should read --oven--. Column 34, line 46, "II" should read --III--; line 64, "terephthalene" should read --terephthalate--; last line, "mg./ft.2" should read --mg./ft.$^2$--.

Column 40, line 13, "$R_4$" should read --$R^4$--. Column 42, approximate columnar line 63, that part of the extreme right portion of the formula reading

UNITED STATES PATENT AND TRADEMARK OFFICE

CERTIFICATE OF CORRECTION

PATENT NO. : 4,108,850

DATED : August 22, 1978

INVENTOR(S) : Fields et al

It is certified that error appears in the above-identified patent and that said Letters Patent are hereby corrected as shown below:

"$(CH_3)_2$" should read --$(CH_3)_3$--; column 43, approximate line 15, that part of the extreme right portion of the formula reading "$(CH_3)_2$" should read --$(CH_3)_3$--.

Signed and Sealed this

*Sixteenth* Day of *October 1979*

[SEAL]

*Attest:*

RUTH C. MASON
*Attesting Officer*

LUTRELLE F. PARKER
*Acting Commissioner of Patents and Trademarks*